(12) United States Patent
Chudzik et al.

(10) Patent No.: US 7,919,111 B2
(45) Date of Patent: *Apr. 5, 2011

(54) BIODEGRADABLE HYDROPHOBIC POLYSACCHARIDE-BASED DRUG DELIVERY IMPLANTS

(75) Inventors: Stephen J. Chudzik, St. Paul, MN (US); Signe R. Erickson, Long Beach, CA (US); Jeffrey J. Missling, Eden Prairie, MN (US)

(73) Assignee: SurModics, Inc., Eden Prairie, MN (US)

( * ) Notice: Subject to any disclaimer, the term of this patent is extended or adjusted under 35 U.S.C. 154(b) by 642 days.

This patent is subject to a terminal disclaimer.

(21) Appl. No.: 11/724,554

(22) Filed: Mar. 15, 2007

(65) Prior Publication Data

US 2007/0224247 A1 Sep. 27, 2007

Related U.S. Application Data

(60) Provisional application No. 60/782,957, filed on Mar. 15, 2006, provisional application No. 60/900,853, filed on Feb. 10, 2007.

(51) Int. Cl.
*A61F 2/02* (2006.01)
(52) U.S. Cl. .................................................. 424/425
(58) Field of Classification Search .................... None
See application file for complete search history.

(56) References Cited

U.S. PATENT DOCUMENTS

| 4,011,392 | A | * | 3/1977 | Rudolph et al. ............... 536/108 |
| 5,459,258 | A | | 10/1995 | Merrill et al. |
| 5,470,581 | A | * | 11/1995 | Grillo et al. .................... 424/479 |
| 5,869,647 | A | | 2/1999 | Narayan et al. |
| 2002/0123624 | A1 | | 9/2002 | Qiao et al. |
| 2004/0037886 | A1 | | 2/2004 | Hsu |
| 2005/0019371 | A1 | | 1/2005 | Anderson et al. |
| 2006/0249705 | A1 | * | 11/2006 | Wang et al. ............. 252/62.51 C |
| 2007/0218102 | A1 | | 9/2007 | Chudzik et al. |
| 2007/0260054 | A1 | | 11/2007 | Chudzik |

FOREIGN PATENT DOCUMENTS

| EP | 0405917 | 1/1991 |
| JP | 2001064157 | 3/2001 |
| WO | WO 02/094224 | 11/2002 |

OTHER PUBLICATIONS

B. van Veen, et al. "The effect of powder blend and tablet structure on drug release mechanisms of hydrophobic starch acetate matrix tablets," European Journal of Pharmaceutics and Biopharmaceutics, 61 (2005) 149-157.

(Continued)

*Primary Examiner* — Carlos A Azpuru
(74) *Attorney, Agent, or Firm* — Kagan Binder, PLLC

(57) ABSTRACT

Medical implants formed of hydrophobic derivatives of natural biodegradable polysaccharides and that include bioactive agent are described. The implants demonstrate desirable bioactive agent release profiles and can be prepared to have high drug loading. The implants can be used to treat medical conditions, such as those requiring prolonged administration of the bioactive agent at a target location in the body.

34 Claims, 8 Drawing Sheets

OTHER PUBLICATIONS

Tarvainen, et al. "Aqueous starch acetate dispersion as a novel coating material for controlled release products," Journal of Controlled Release, 96 (2004) 179-191.

Magdassi, et al. "Interfacial Properties of Hydrophobically Modified Biomolecules: Fundamental Aspects and Applications," J. Dispersion Science and Technology, 22(4), 313-322 (2001).

Na, K., et al. "Self-assembled nanoparticles of hydrophobically-modified polysaccharide bearing vitamin H as a targeted anti-cancer drug delivery system," European Journal of Pharmaceutical Sciences, 18 (2003) 165-173.

Uekama, K., "Pharmaceutical Application of Cyclodextrins as Multifunctional Drug Carriers," Yakugaku Zasshi, 124(12) 909-935 (2004).

Kaur, I.P., et al., "Role of Cyclodextrins in Ohpthalmics," Current Drug Delivery, 2004, I, 351-360.

* cited by examiner

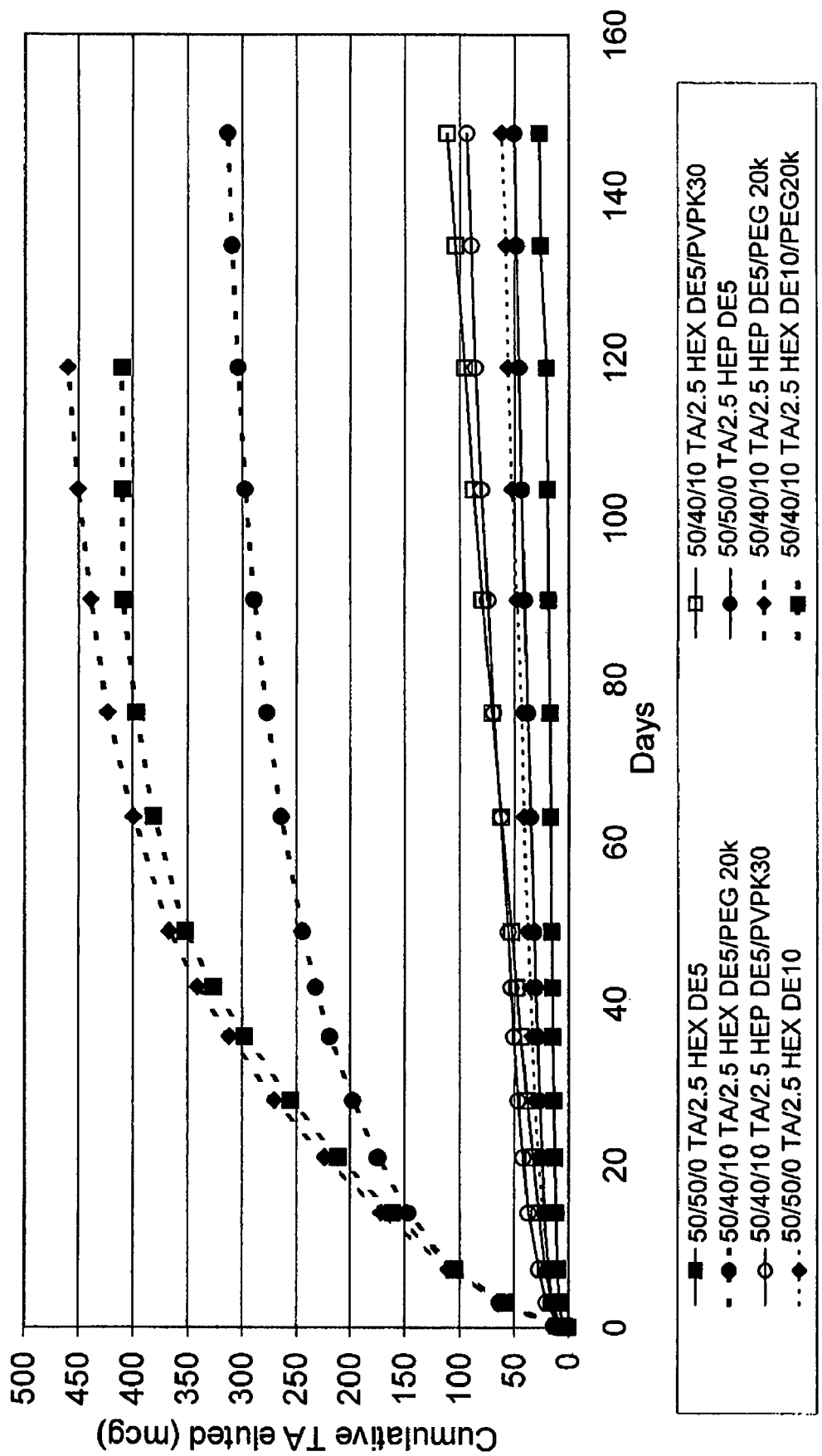

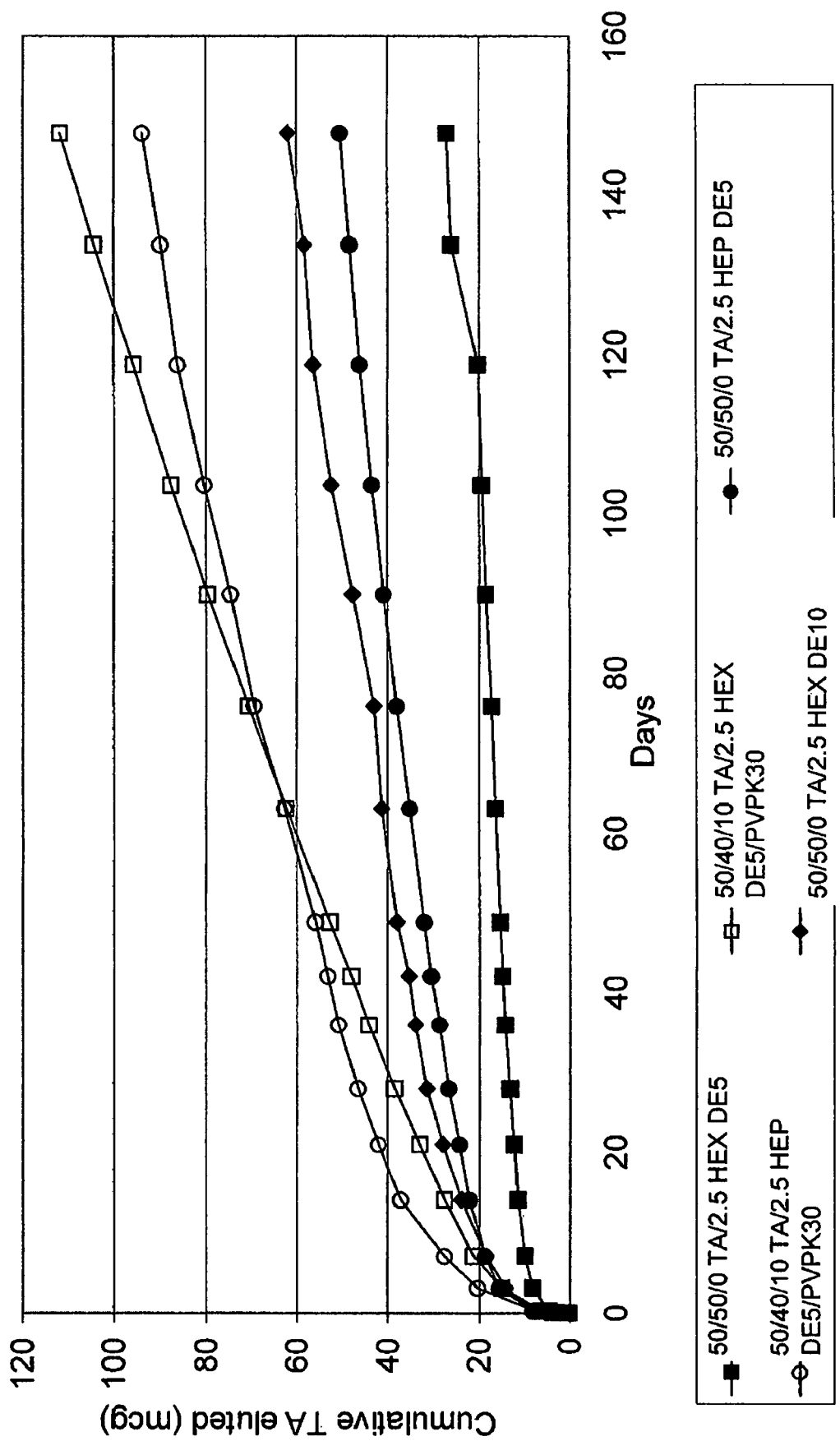

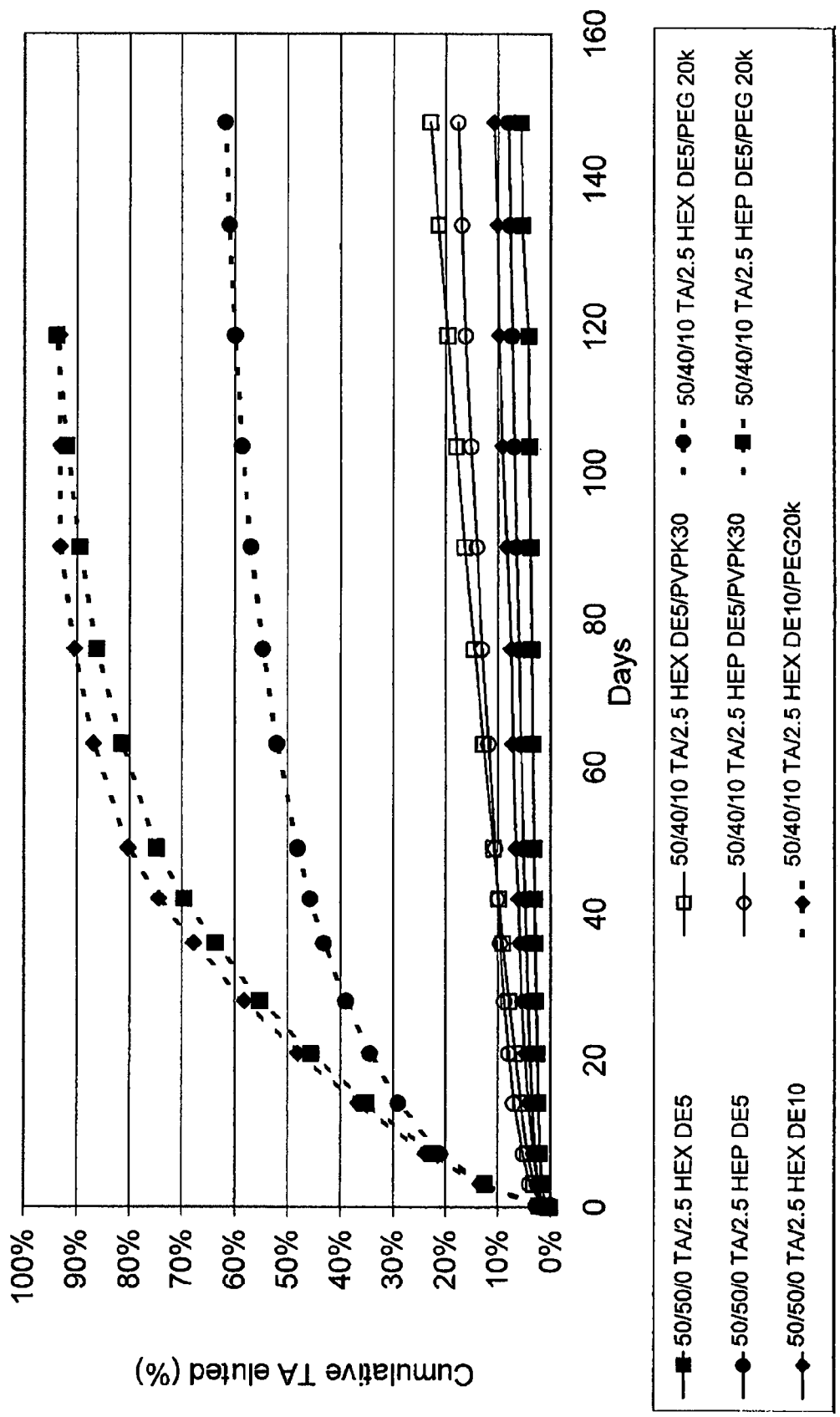

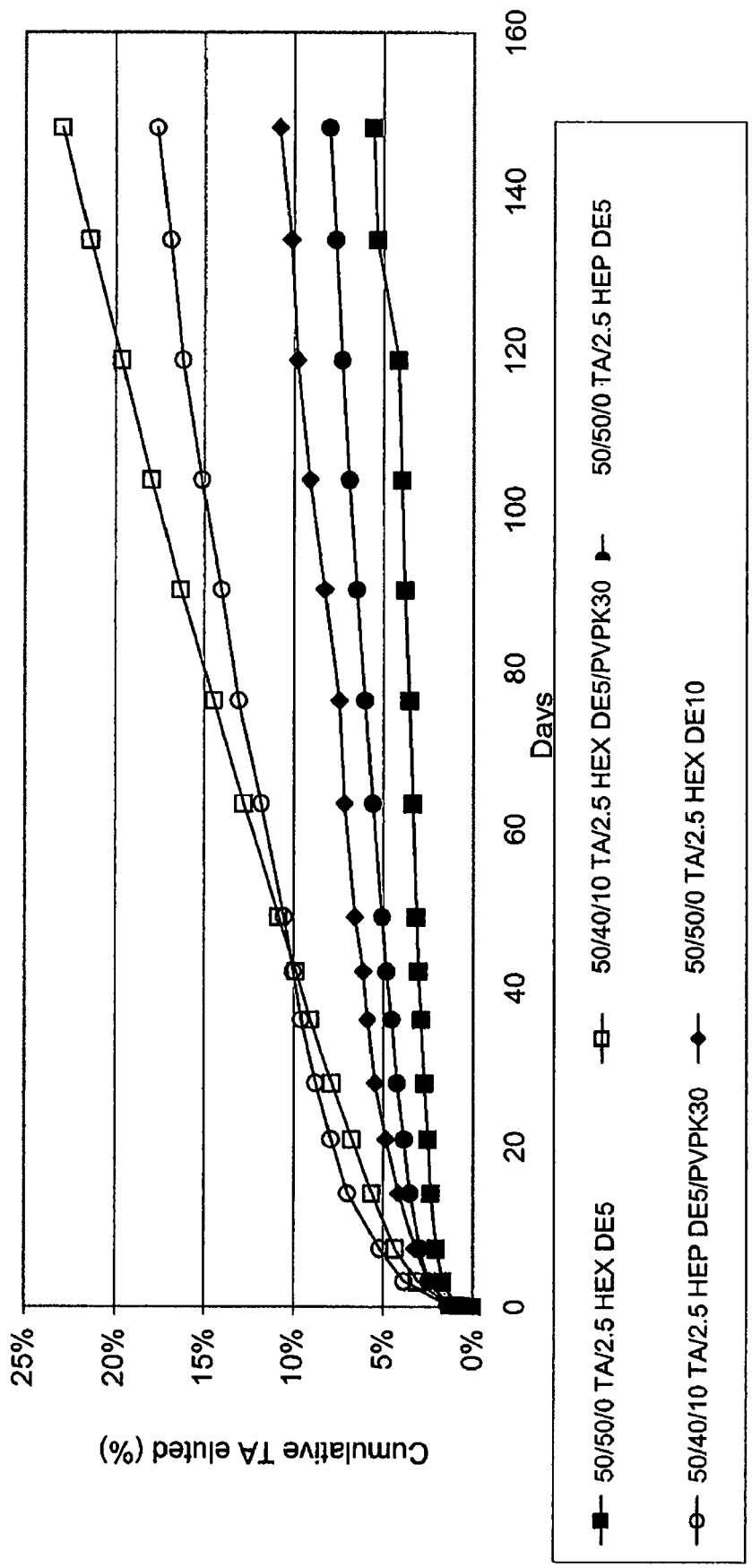
Figure 2B: TA Release in PBS pH 7.4 at 37C
Pellet Spefication: 5mm long, 0.5 mm diameter, 500 mcg TA load

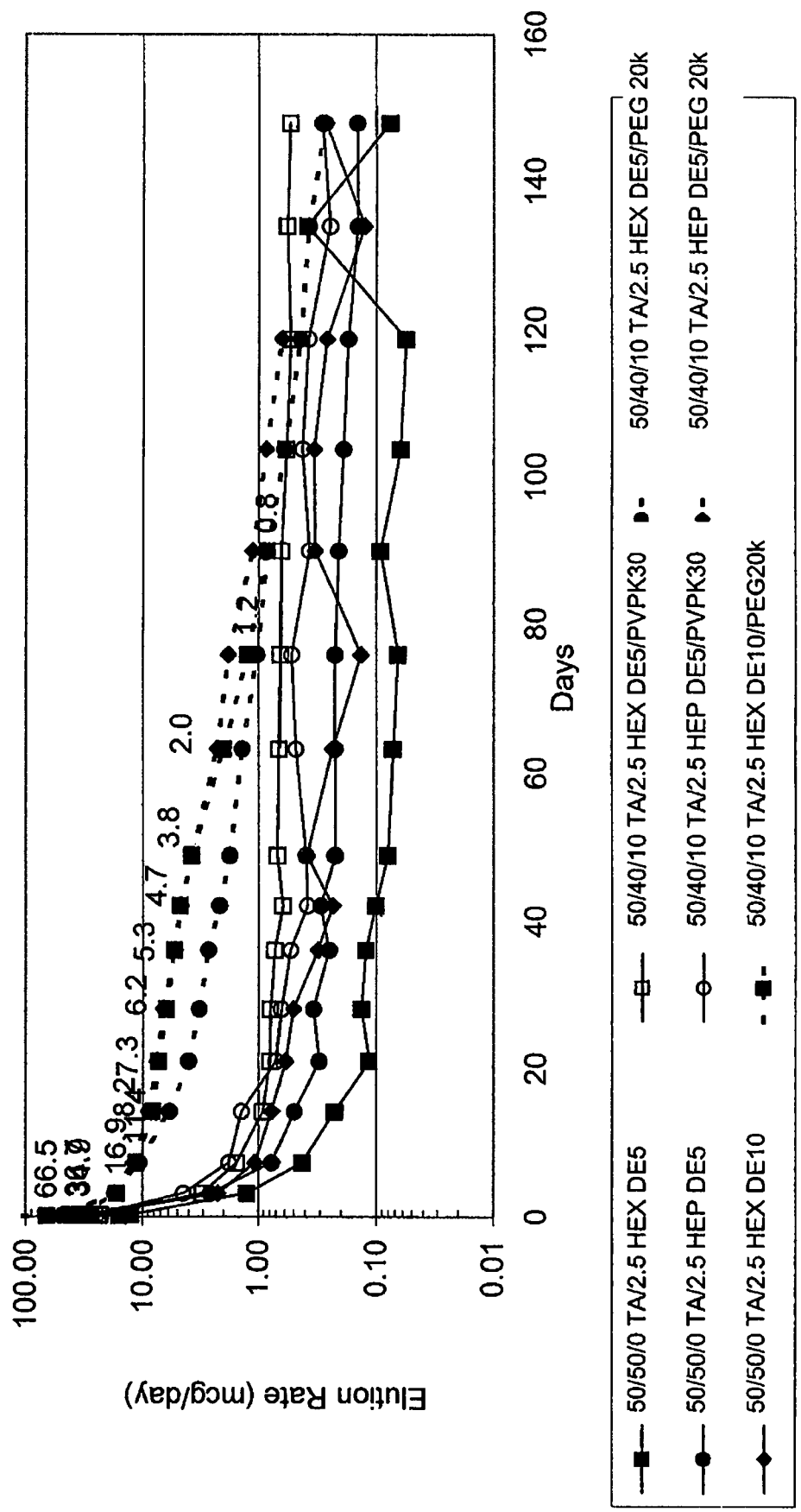

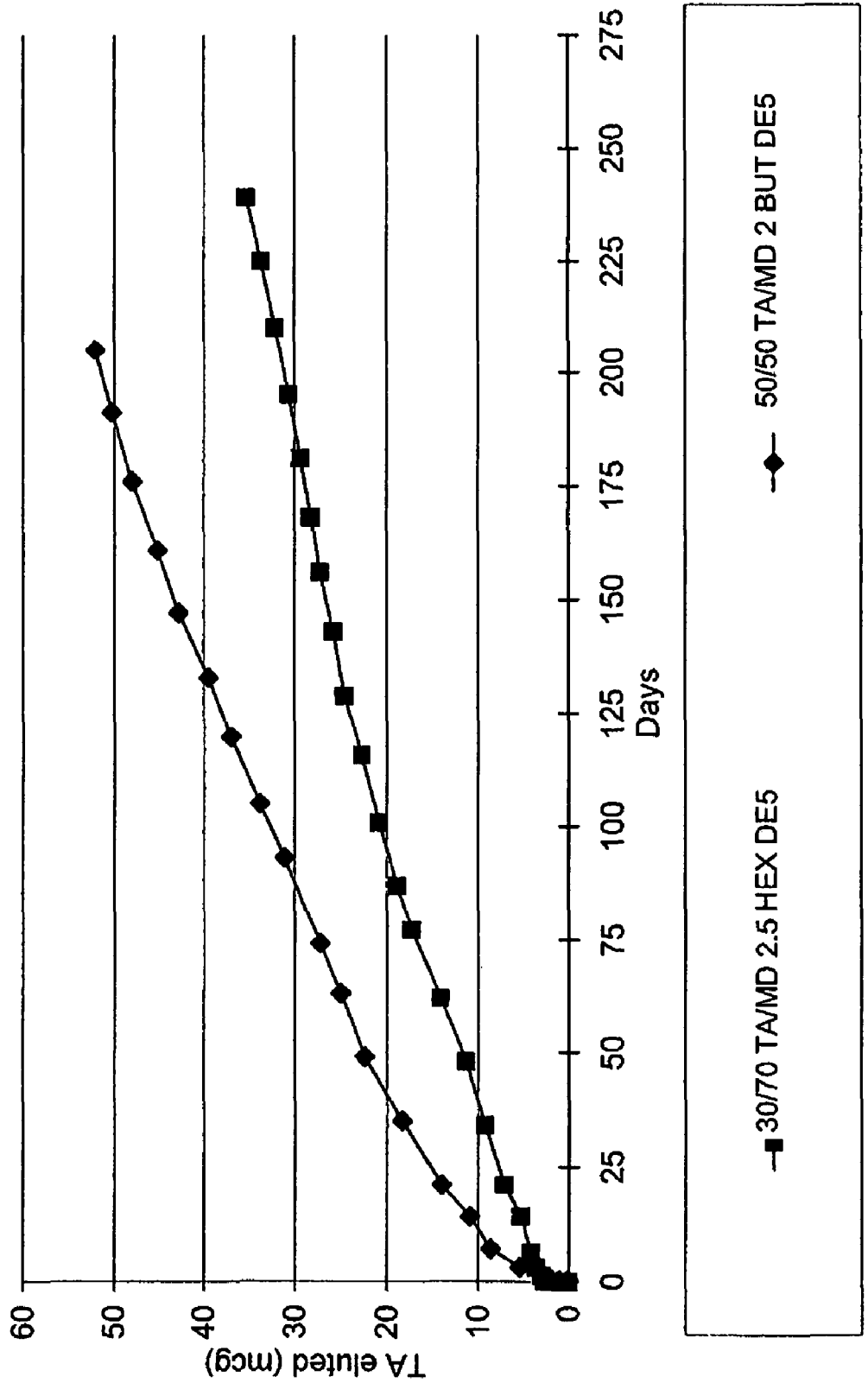
Figure 4A: TA Release in PBS pH 7.4 at 37C 5mm long, 0.5 mm diameter, 1 mg total weight (300 or 500 ug drug load)

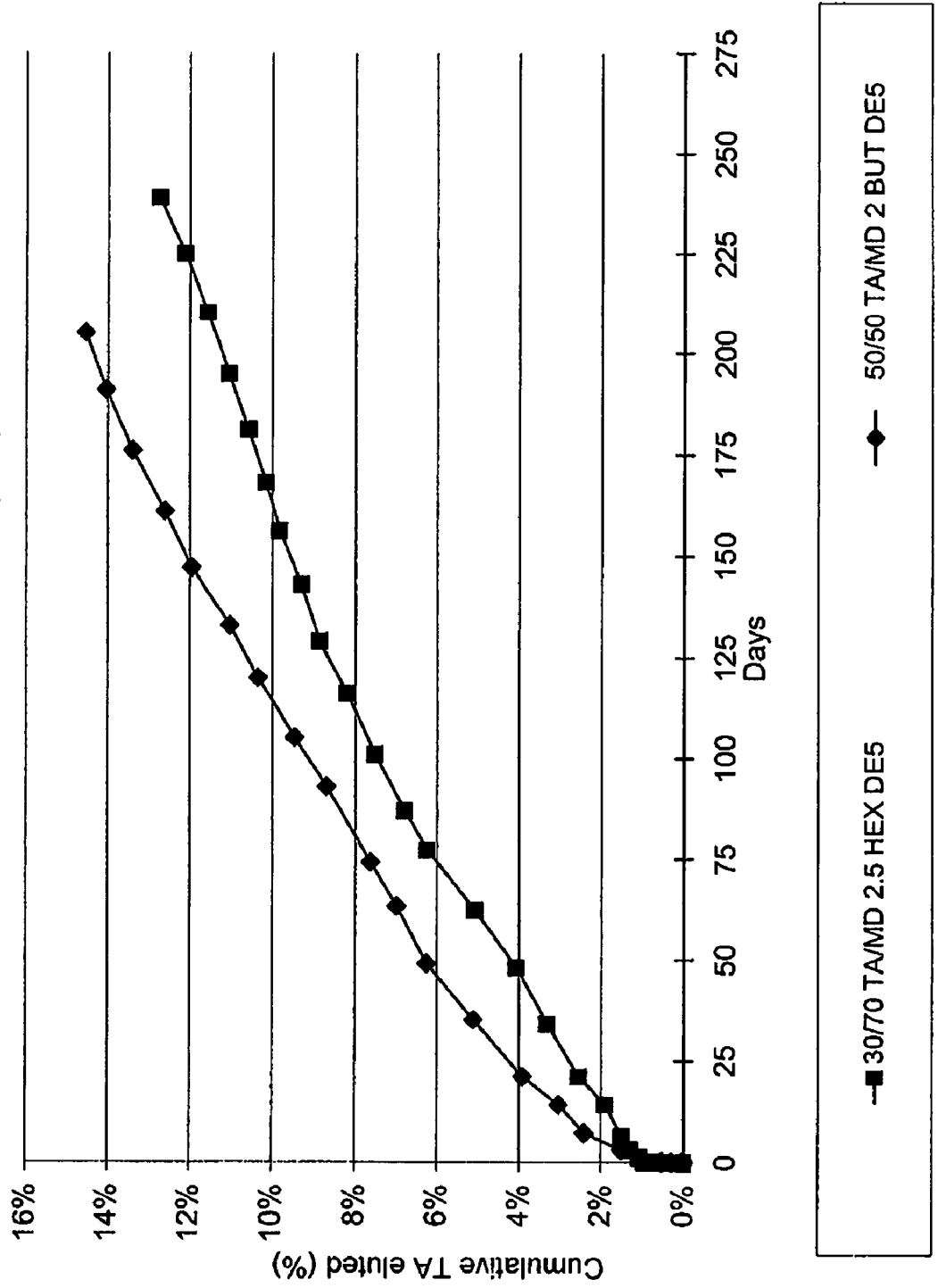

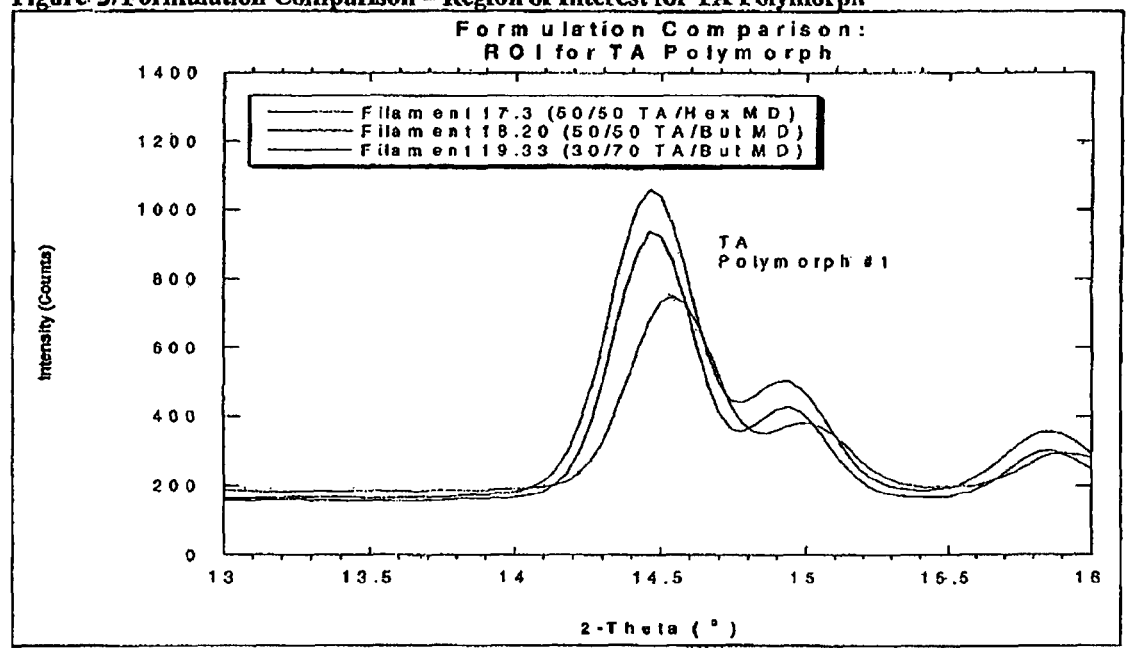
Figure 5: Formulation Comparison – Region of Interest for TA Polymorph

BIODEGRADABLE HYDROPHOBIC POLYSACCHARIDE-BASED DRUG DELIVERY IMPLANTS

CROSS-REFERENCE TO RELATED APPLICATIONS

The present non-provisional Application claims the benefit of commonly owned provisional Application having Ser. No. 60/782,957, filed on Mar. 15, 2006, and entitled HYDROPHOBIC DERIVATIVES OF NATURAL BIODEGRADABLE POLYSACCHARIDES; and commonly owned provisional Application having Ser. No. 60/900,853, filed on Feb. 10, 2007, and entitled BIODEGRADABLE HYDROPHOBIC POLYSACCHARIDE-BASED DRUG DELIVERY IMPLANTS; which Applications are incorporated herein by reference in their entirety.

TECHNICAL FIELD

The present invention relates to drug-releasing medical implants formed of a biodegradable material, and methods for preparing the implants. The invention also relates to the treatment of medical conditions, such as ocular diseases.

BACKGROUND

In recent years, much attention has been given to site-specific delivery of drugs within a patient. Although various drugs have been developed for treatment of a wide variety of ailments and diseases of the body, in many instances, such drugs cannot be effectively administered systemically without risk of detrimental side effects. Site-specific drug delivery focuses on delivering the drugs locally, i.e., to the area of the body requiring treatment. One benefit of the local release of bioactive agents is the avoidance of toxic concentrations of drugs that are at times necessary, when given systemically, to achieve therapeutic concentrations at the site where they are required.

Site-specific drug delivery can be accomplished by injection and/or implantation of an article or device that releases the drug to the treatment site. Injection of drugs can have limitations, for example, by requiring multiple administrations, increasing risk of complications (such as infection), and patient discomfort. Implantation of an article or device that delivers drug to the treatment site has therefore gained much interest in recent years.

Further, site-specific drug delivery has been enhanced by technologies that allow controlled release of one or more drugs from an implanted article. Controlled release can relate to the duration of time drug is released from the device or article, and/or the rate at which the drug is released.

Several challenges confront the use of medical devices or articles that release bioactive agents into a patient's body. For example, treatment may require release of the bioactive agent(s) over an extended period of time (for example, weeks, months, or even years), and it can be difficult to sustain the desired release rate of the bioactive agent(s) over such long periods of time.

While advances in site-specific implantable drug delivery systems have been made, many systems do not release drug in a desired manner following implantation in a patient. For example, in many systems the majority of the drug present in the article is released from the device in an initial burst, resulting in premature depletion of the drug. Following this depletion, the drug may be delivered to the subject in suboptimal amounts.

In other systems, such as those based on polylactide-type biodegradable polymers, the majority of drug may be released at later points during the administration period due to bulk erosion of the drug containing biodegradable matrices.

If drug is prematurely released from the implant, or not released until later, the duration of treatment or the rate of release may not be as long as desired. This can cause the implant to be therapeutically less effective.

In addition, many drug delivery systems may demonstrate a great variation in the rate of drug release over the period of implantation. In these cases, an optimal rate of drug release may be seen only during a very small window over the period of implantation.

Other concerns regarding medical implants relate to biocompatibility. If materials that are used to prepare the implant promote an adverse tissue response in the body, the effectiveness of the implant can be reduced.

For example, as an alternative to non-biodegradable systems, synthetic biodegradable polymers, such as polyglycolide-type molecules, have been used for the construction of implantable medical devices and for delivery of bioactive agents. These types of biodegradable materials have the potential to degrade into products that cause unwanted side effects in the body by virtue of their presence or concentration in vivo. These unwanted side effects can include immune reactions, toxic buildup of the degradation products in the body, or the initiation or provocation of other adverse effects on cells or tissue in the body.

SUMMARY OF THE INVENTION

Generally, the present invention relates to biodegradable implants for the delivery of one or more bioactive agents to a subject. The implants include a matrix formed of hydrophobic natural biodegradable polysaccharides and bioactive agent within the matrix, wherein the bioactive agent is releasable from the matrix upon implantation in a subject. The present invention also relates to treating medical conditions using the implants of the present invention. Furthermore, the present invention relates to methods for forming the implant using a process which maintains desirable properties of the bioactive agent, thereby providing a more therapeutically effective implant.

According to the materials and methods described herein, biodegradable implants were prepared and tested for bioactive agent release. Results of the experimental studies of the present invention showed that bioactive agent was released from the implants in therapeutically effective ranges and for therapeutically effective periods of time. In view of this, the implants can be used for the site-specific treatment of any one of a variety of medical conditions.

Results also showed the biodegradable implants provided a moderate or minimal initial burst of bioactive agent, and no late stage burst. This is beneficial, as depletion of substantial amounts of bioactive agent from the implant at an early stage following implantation can be avoided.

The medical implants were also fabricated having a high drug loading capacity, but were still able to release the bioactive agent at a steady, therapeutically effective rate. This allows the implants to be useful for the prolonged release of bioactive agents to treat medical conditions. For example, in some cases the implants can be formed to release the bioactive agent in a therapeutically useful amount for a period of time greater than one month, three months, six months, or even a year. Given the prolonged release of bioactive agent, the need for periodic administration of the bioactive agent is not required. This is beneficial as it eliminates or significantly reduces need for patient compliance.

In addition, it was found that changes to the biodegradable polysaccharide chemistry and/or polymer composition could be made to alter the release rate of the bioactive agent within therapeutically useful ranges. This "tunability" of bioactive release represents an advantage in the design and use of biodegradable medical implants, as specific daily doses of bioactive agent can be provided to a subject.

In one aspect, the invention provides a bioactive-agent releasing biodegradable medical implant comprising a matrix of hydrophobic natural biodegradable polysaccharides and a bioactive-agent within the matrix, wherein the bioactive agent is capable of being released from the implant upon placement in a subject. Preferably, the implants of the present invention include hydrophobic derivatives of lower molecular weight natural biodegradable polysaccharides, wherein the hydrophobic derivatives have a molecular weight of about 500,000 Da or less. Even more preferably are hydrophobic derivatives having a molecular weight of about 100,000 Da or less, 50,000 Da or less, 25,000 Da or less, or in the range of 2000 Da to about 20,000 Da.

In some aspects, the implants are formed from low molecular weight hydrophobic derivatives of $\alpha$-1,4 glucopyranose polymers. For example, the implants can be formed from a polymer selected from hydrophobic derivatives of maltodextrin, polyalditol, amylose, and cyclodextrin polymers. Degradation of a natural biodegradable polysaccharide-containing ocular implant can result in the release of, for example, naturally occurring mono- or disaccharides, such as glucose, which are common components of bodily fluids. Given this, the implants of the invention have improved biocompatibility.

The hydrophobic derivatives of the biodegradable polysaccharides can include groups that are pendent from the polysaccharide backbone which provide the hydrophobic portion. In some aspects, the pendent groups can comprise a hydrocarbon segment that is a linear, branched, or cyclic $C_2$-$C_{18}$ group. In some aspects the pendent groups can comprise a hydrocarbon segment that is a linear, branched, or cyclic $C_2$-$C_{10}$ group, or a linear, branched, or cyclic $C_4$-$C_8$ group. In many aspects, the linkage between the pendent group and polysaccharide backbone includes a cleavable covalent bond, such as an ester bond that can be cleaved by hydrolysis.

Release rate of the bioactive agent can be affected in one or more ways. For example, an increase in the size of the alkyl group generally lowers the Tg of the hydrophobic polysaccharide and increases the release rate of bioactive agent from the implant. A decrease in the size of the alkyl group generally increases the Tg of the hydrophobic polysaccharide and decreases the release rate. In some aspects the hydrophobic polysaccharide has a glass transition temperature ($T_g$) of about 35° C. or greater, about 40° C. or greater, such as in the range of about 40° C. to about 65° C., or more specifically in the range of about of 40° C. to about 60° C.

In some aspects, the biodegradable implant includes a hydrophilic biocompatible polymer. A hydrophilic biocompatible polymer can increase the rate of release of bioactive agent from the medical implants. In some aspects, the hydrophilic polymer is selected from the group consisting of poly (ethylene glycol), hydrophilic polysaccharides, polyvinyl pyrrolidones, polyvinyl alcohols, low molecular weight methyl cellulose, hydroxypropyl methyl cellulose (HPMC), and the like. In some aspects, the implant comprises up to about 10% wt of the hydrophilic biocompatible polymer.

Various types of bioactive agents can be delivered from the implant. Exemplary bioactive agents include, anti-proliferative agents, anti-inflammatory agents, angiogenesis inhibitors, neuroprotective agents, beta adrenergic agents, prostaglandins, or combinations thereof.

In some aspects, bioactive agent is present in an amount up to about 65 wt % of the implant, such as in the range of about 10 wt % to about 65 wt %, up to about 55% wt, such as in the range of about 25 wt % to about 55 wt %, or about 40 wt % to about 50 wt %.

Given the high drug loading capacity, particularly small implants capable of delivering a therapeutically effective dose of bioactive agent were prepared. Use of small implants is beneficial such as it can reduce the invasiveness of an implantation procedure. In addition, the small size permits placement in limited access regions of the body, such as the eye.

In one specific embodiment, the implant comprises a length of about 5 mm or less. In another specific embodiment, the implant comprises a diameter of about 0.5 mm or less. For example, the implant can have a cylindrical or rod-like shape, and the diameter of the implant is about 0.5 mm or less. In one specific embodiment, the implant comprises a diameter of about 0.35 mm or less, and a length of about 4 mm or less.

In some aspects the implant has a volume of greater than about 0.53 $mm^3$. In some aspects, the volume is in the range of about 0.75 $mm^3$ to about 2.5 $mm^3$.

In another specific embodiment, the implant has a weight of about 6 mg or less. In another specific embodiment, the implant has a weight of about 2.5 mg or less, or about 1 mg or less.

In other embodiments, the implant is in the form of microparticulates.

In another aspect, the invention provides a method for delivering a bioactive agent to a subject. The method includes a step of implanting at a target site in a subject a bioactive-agent releasing biodegradable medical implant comprising a matrix of hydrophobic natural biodegradable polysaccharides and a bioactive-agent, which is within the matrix. The method also includes a step of allowing the bioactive agent to be released from the implant following delivery to a target location in the subject.

The implants of the invention can release bioactive agent in a therapeutically effective range, such as an amount of nanograms per day, up to about tens of micrograms per day. In some aspects, the bioactive agent is released in an amount in the range of about 0.1 microgram per day to about 10 micrograms per day.

In some specific aspects, the method for delivering a bioactive agent to a subject is performed for the treatment of an ocular condition or indication. In the step of implanting, an ocular implant in implanted at a location in the eye. The ocular implant is maintained in the eye for a period of time sufficient for the treatment of the ocular condition of indication.

In some aspects, the step of implanting comprises placing the implant in contact with retinal tissue. For example, the method can include providing the implant to a subretinal location. In another aspect, the step of implanting comprises placing the implant in the vitreous. In another aspect, the step of implanting comprises placing the implant subconjuntivally (e.g., at an extrascleral location). In another aspect, the step of implanting comprises placing the implant in the cul de sac (e.g., at an extraocular location). In another aspect, the step of implanting comprises placing the implant in the anterior chamber of the eye.

In many cases, the small size of the implant allows the method to be performed without requiring additional procedures, such as suturing of the sclera. In some aspects the ocular implant is implanted in the eye using an insertion tool comprising a needle having a size of 25 gauge or smaller.

The ocular implant can release the bioactive agent over a prolonged period of time to treat the ocular condition or indication. For example, the ocular implant can be maintained in the eye for a period of about three months or greater to provide treatment to the eye. The lifetime of the ocular implant may be greater than three months, such as in the range of about three to about eighteen months.

The ocular condition or indication can be one or more selected from retinal detachment; vascular occlusions; retinitis pigmentosa; proliferative vitreoretinopathy; diabetic retinopathy; inflammations such as uveitis, choroiditis, and retinitis; glaucoma; degenerative disease (such as age-related macular degeneration, also referred to as AMD); vascular diseases; and various tumor-related conditions, including those associated with neoplasms.

The invention also relates to methods for preparing medical implants. In particular, the hydrophobic polysaccharide materials of the present invention permit the implant to be prepared in a process that maintains properties of the bioactive agent during the process of forming the implant. In particular, the invention provides a solventless process for preparing the implants.

The method comprises a step of obtaining a bioactive agent in a first polymorphic form. Next, a composition comprising hydrophobic natural biodegradable polysaccharide and the bioactive-agent is prepared, wherein the composition does not include a solvent. The composition is then heated to provide a liquefied composition. After heating, the liquefied composition is formed into a shape of a medical implant.

The use of solvents may otherwise cause crystallization of the bioactive agent and generate other polymorphic forms of the bioactive agent. In some specific aspects, step of obtaining comprises obtaining a bioactive agent in a first polymorphic form. In the steps of heating and forming, there is substantially none, or no conversion of the bioactive agent from the first polymorphic form to a polymorphic form that is different than the first polymorphic form.

In some specific aspects, the composition is heated to a temperature in the range of about 80° C. to about 100° C. and then subjected to an extrusion or molding process.

BRIEF DESCRIPTION OF THE DRAWINGS

FIG. 1A is a graph illustrating cumulative amounts of triamcinolone acetonide released (μg) from hydrophobic maltodextrin-based pellets and hydrophobic maltodextrin-based pellets with biocompatible hydrophilic polymeric (PEG or PVP) additives, as measured during 120 day and 150 day elution periods in vitro.

FIG. 1B is a portion of the graph of FIG. 1A showing in greater detail cumulative amounts of triamcinolone acetonide released (μg) from the slower releasing hydrophobic maltodextrin-based pellets and hydrophobic maltodextrin-based pellets with the PVP additive, as measured during 150 day elution periods in vitro.

FIG. 2A is a graph illustrating cumulative amounts of triamcinolone acetonide released (based on the % of the total amount of triamcinolone per pellet) from the hydrophobic maltodextrin-based pellets and hydrophobic maltodextrin-based pellets with biocompatible hydrophilic polymeric (PEG or PVP) additives (of FIG. 1A), as measured during 120 day and 150 day elution periods in vitro.

FIG. 2B is a portion of the graph of FIG. 2B showing in greater detail cumulative amounts of triamcinolone acetonide released (based on the % of the total amount of triamcinolone per pellet) from the slower eluting hydrophobic maltodextrin-based pellets and hydrophobic maltodextrin-based pellets with the PVP additive, as measured during 150 day elution periods in vitro.

FIG. 3 is a graph illustrating release rates (μg/day) of triamcinolone acetonide from hydrophobic maltodextrin-based pellets and hydrophobic maltodextrin-based pellets with biocompatible hydrophilic polymeric (PEG or PVP) additives (of FIG. 1A), as measured during 120 day and 150 day elution periods in vitro.

FIG. 4A is a graph illustrating cumulative release of triamcinolone acetonide (μg) from hydrophobic maltodextrin-based pellets, as measured during 210 day and 240 day elution periods in vitro.

FIG. 4B is a graph illustrating cumulative release of triamcinolone acetonide (based on the % of the total amount of triamcinolone per pellet) from hydrophobic maltodextrin-based pellets, as measured during 210 day and 240 day elution periods in vitro.

FIG. 5 is a graph of an X-ray diffraction (XRD) spectra of various hydrophobic maltodextrin-based pellets showing peaks corresponding to non-polymorphic and polymorphic fauns of triamcinolone acetonide in the pellets.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention is generally directed to medical implants having a matrix comprising hydrophobic derivatives of natural biodegradable polysaccharides, and bioactive agent that is contained within and releasable from the matrix following implantation in a patient. The invention is also directed to methods for delivering bioactive agents to a subject from the medical implants of the invention. The invention is further directed to methods for preparing the medical implants of the invention.

As used herein, the term "medical implant" refers to an article that is designed to be placed at a target location in the body and reside at that target location for a period of time. The medical implants of the invention are also bioactive-agent releasing and biodegradable.

The medical implants of the invention can be of any shape or size to suitably reside at a target site in the body following implantation. For example, the implant can be in the form of rods, pellets, disks, spheres, strips, coils, etc. The implant can be microparticle sized or larger. The implant can be used in combination with implants that are of different size and shapes. As an example, the implant can include a set of various sized and shaped microparticulates.

The medical implants have an in vivo lifetime, which is a period of time starting upon implant placement at the target location, and ending when the implant is completely degraded at the target location. The bioactive agent can be released from the implant during the entire in vivo lifetime, or during a portion of the implant's in vivo lifetime. The period of time in which the bioactive agent is released from the implant is referred to as the "bioactive agent release period." If the bioactive agent release period is less than the in vivo lifetime of the implant, the bioactive agent is generally released from the implant at a rate faster than loss and/or degradation of the hydrophobic polysaccharide from the implant. In this case, release of the bioactive agent out of the implant, such as by diffusion, may cause the bioactive agent release period to be less than the in vivo lifetime of the implant.

A "subject" refers to an organism in which the medical implant is placed and which the bioactive agent becomes available in following implantation. The subject can be a patient having a medical condition, wherein the condition is treatable using a bioactive agent that is released from the medical implants of the invention. The subject can be a human, another mammal, or a non-mammalian organism. For example, the subject can be a domesticated mammal such as a dog, cat, horse, cow, sheep, rabbit, etc. The subject can also be a bird, fish, or reptile.

The medical implant includes a matrix of hydrophobic derivatives of natural biodegradable polysaccharides. The matrix is formed via hydrophobic interactions of the hydrophobic portion of the polysaccharide, and bioactive agent held within the matrix. The bioactive agent is released from the implant after the implant is delivered to a target location in the body.

As used herein, a "hydrophobic derivative" of a natural biodegradable polysaccharide refers to a natural biodegradable polysaccharide having one or more pendent groups attached to the polysaccharide. In many cases the hydrophobic derivative includes a plurality of groups comprising hydrocarbon segments attached to the polysaccharide. When a plurality of groups comprising hydrocarbon segments is attached they are collectively referred to as the "hydrophobic portion" of the hydrophobic derivative. The hydrophobic derivatives of the invention therefore include a hydrophobic portion and a polysaccharide portion.

The implant of the present invention is described as being formed from a "matrix" of hydrophobic derivative of a natural biodegradable polysaccharide. Generally, the matrix provides the structural framework of the implant, which is established by association of the hydrocarbon segments of the groups pendent from the polysaccharides. The structural integrity of the implant can therefore be in part based on the hydrophobic interactions in the matrix. Optionally, the matrix can include other types of non-hydrophobic associations between polysaccharides, such as covalent or non-covalent crosslinks which may be formed by groups pendent from the polysaccharide or groups independent of the polysaccharide.

The polysaccharide portion comprises a "natural biodegradable polysaccharide," which refers to a non-synthetic polysaccharide that is capable of being enzymatically degraded. Natural biodegradable polysaccharides include polysaccharide and/or polysaccharide derivatives that are obtained from natural sources, such as plants or animals. Natural biodegradable polysaccharides include any polysaccharide that has been processed or modified from a natural biodegradable polysaccharide (for example, maltodextrin is a natural biodegradable polysaccharide that is processed from starch). Exemplary natural biodegradable polysaccharides include maltodextrin, amylose, cyclodextrin, polyalditol, hyaluronic acid, dextran, heparin, chondroitin sulfate, dermatan sulfate, heparan sulfate, keratan sulfate, dextran, dextran sulfate, pentosan polysulfate, and chitosan. Preferred polysaccharides are low molecular weight polymers that have little or no branching, such as those that are derived from and/or found in starch preparations, for example, maltodextrin, amylose, and cyclodextrin. Therefore, the natural biodegradable polysaccharide can be a substantially non-branched or completely non-branched poly(glucopyranose) polymer.

As used herein, "amylose" or "amylose polymer" refers to a linear polymer having repeating glucopyranose units that are joined by α-1,4 linkages. Some amylose polymers can have a very small amount of branching via α-1,6 linkages (about less than 0.5% of the linkages) but still demonstrate the same physical properties as linear (unbranched) amylose polymers do. Generally amylose polymers derived from plant sources have molecular weights of about $1 \times 10^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of $1 \times 10^7$ Da or greater.

Amylose can be obtained from, or is present in, a variety of sources. Typically, amylose is obtained from non-animal sources, such as plant sources. In some aspects, a purified preparation of amylose is used as starting material for the preparation of the amylose polymer having pendent groups comprising hydrocarbon segments. In other aspects, as starting material, amylose can be used in a mixture that includes other polysaccharides.

For example, in some aspects, starch preparations having a high amylose content, purified amylose, synthetically prepared amylose, or enriched amylose preparations can be used in the preparation of a hydrophobic derivative of amylose. In starch sources, amylose is typically present along with amylopectin, which is a branched polysaccharide. If a mixture of amylose and a higher molecular weight precursor is used (such as amylopectin), it is preferred that amylose is present in the composition in an amount greater than the higher molecular weight precursor. For example, in some aspects, starch preparations having high amylose content, purified amylose, synthetically prepared amylose, or enriched amylose preparations can be used in the preparation of a hydrophobic derivative of amylose polymer. In some embodiments the composition includes a mixture of polysaccharides including amylose wherein the amylose content in the mixture of polysaccharides is 50% or greater, 60% or greater, 70% or greater, 80% or greater, or 85% or greater by weight. In other embodiments the composition includes a mixture of polysaccharides including amylose and amylopectin and wherein the amylopectin content in the mixture of polysaccharides is 30% or less, or 15% or less.

The amount of amylopectin present in a starch may also be reduced by treating the starch with amylopectinase, which cleaves α-1,6 linkages resulting in the debranching of amylopectin into amylose.

Steps may be performed before, during, and/or after the process of derivatizing the amylose polymer with groups comprising hydrocarbon segments to enrich the amount of amylose, or purify the amylose.

Amylose of particular molecular weights can be obtained commercially or can be prepared. For example, synthetic amyloses with average molecular masses of 70 kDa, 110 kDa, and 320 kDa, can be obtained from Nakano Vinegar Co., Ltd. (Aichi, Japan). The decision of using amylose of a particular size range may depend on factors such as the physical characteristics of the composition (e.g., viscosity), the desired rate of degradation of the article formed from the hydrophobic derivative, and the presence of other optional components in the composition, such as bioactive agents.

Purified or enriched amylose preparations can be obtained commercially or can be prepared using standard biochemical techniques such as chromatography. In some aspects, high-amylose cornstarch can be used to prepare the hydrophobic derivative.

Maltodextrin is typically generated by hydrolyzing a starch slurry with heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate X 100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights, for example, in the range of about 500 Da to 5000 Da are commercially available (for example, from CarboMer, San Diego, Calif.).

Another contemplated class of natural biodegradable polysaccharides is natural biodegradable non-reducing polysaccharides. A non-reducing polysaccharide can provide an inert matrix thereby improving the stability of sensitive bioactive agents, such as proteins and enzymes. A non-reducing polysaccharide refers to a polymer of non-reducing disaccharides (two monosaccharides linked through their anomeric centers) such as trehalose (α-D-glucopyranosyl α-D-glucopyranoside) and sucrose (β-D-fructofuranosyl α-D-glucopyranoside). An exemplary non-reducing polysaccharide comprises polyalditol which is available from GPC (Muscatine, Iowa). In another aspect, the polysaccharide is a glucopyranosyl polymer, such as a polymer that includes repeating (1→3)O-β-D-glucopyranosyl units.

Dextran is an α-D-1,6-glucose-linked glucan with side-chains 1-3 linked to the backbone units of the dextran biopolymer. Dextran includes hydroxyl groups at the 2, 3, and 4 positions on the glucopyranose monomeric units. Dextran can be obtained from fermentation of sucrose-containing media by *Leuconostoc mesenteroides* B512F.

Dextran can be obtained in low molecular weight preparations. Enzymes (dextranases) from molds such as *Penicillium* and *Verticillium* have been shown to degrade dextran. Similarly many bacteria produce extracellular dextranases that split dextran into low molecular weight sugars.

Chondroitin sulfate includes the repeating disaccharide units of D-galactosamine and D-glucuronic acid, and typically contains between 15 to 150 of these repeating units. Chondroitinase AC cleaves chondroitin sulfates A and C, and chondroitin.

Hyaluronic acid (HA) is a naturally derived linear polymer that includes alternating β1,4-glucuronic acid and β1,3-N-acetyl-D-glucosamine units. HA is the principal glycosaminoglycan in connective tissue fluids. HA can be fragmented in the presence of hyaluronidase.

In many aspects the polysaccharide portion and the hydrophobic portion comprise the predominant portion of the hydrophobic derivative of the natural biodegradable polysaccharide. Based on a weight percentage, the polysaccharide portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. Likewise, based on a weight percentage of the overall hydrophobic derivative, the hydrophobic portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. In exemplary aspects, the hydrophobic derivative has approximately 50% of its weight attributable to the polysaccharide portion, and approximately 50% of its weight attributable to its hydrophobic portion.

The hydrophobic derivative has the properties of being insoluble in water. The term for insolubility is a standard term used in the art, and meaning 1 part solute per 10,000 parts or greater solvent. (see, for example, Remington: The Science and Practice of Pharmacy, 20th ed. (2000), Lippincott Williams & Wilkins, Baltimore Md.).

A hydrophobic derivative can be prepared by associating one or more hydrophobic compound(s) with a natural biodegradable polysaccharide polymer. Methods for preparing hydrophobic derivatives of natural biodegradable polysaccharides are described herein.

The hydrophobic derivatives of the natural biodegradable polysaccharides preferably have a molecular weight of 500,000 Da or less. Use of these lower molecular weight derivatives provides implants with desirable physical and drug-releasing properties. In some aspects the hydrophobic derivatives have a molecular weight of about 250,000 Da or less, about 100,000 Da or less, about 50,000 Da or less, or 25,000 Da or less. Particularly preferred size ranges for the natural biodegradable polysaccharides are in the range of about 2,000 Da to about 20,000 Da, or about 4,000 Da to about 10,000 Da.

The molecular weight of the polymer is more precisely defined as "weight average molecular weight" or $M_w$. $M_w$ is an absolute method of measuring molecular weight and is particularly useful for measuring the molecular weight of a polymer (preparation). Polymer preparations typically include polymers that individually have minor variations in molecular weight. Polymers are molecules that have a relatively high molecular weight and such minor variations within the polymer preparation do not affect the overall properties of the polymer preparation. The weight average molecular weight ($M_w$) can be defined by the following formula:

$$M_W = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W. (1990) *Contemporary Polymer Chemistry*; pg 271.

The addition of hydrophobic portion will generally cause an increase in molecular weight of the polysaccharide from its underivatized, starting molecular weight. The amount increase in molecular weight can depend on one or more factors, including the type of polysaccharide derivatized, the level of derivation, and, for example, the type or types of groups attached to the polysaccharide to provide the hydrophobic portion.

In some aspects, the addition of hydrophobic portion causes an increase in molecular weight of the polysaccharide of about 20% or greater, about 50% or greater, about 75% or greater, about 100% or greater, or about 125%, the increase in relation to the underivatized form of the polysaccharide.

As an example, a maltodextrin having a starting weight of about 3000 Da is derivatized to provide pendent hexanoate groups that are coupled to the polysaccharide via ester linkages to provide a degree of substitution (DS) of about 2.5. This provides a hydrophobic polysaccharide having a theoretical molecular weight of about 6000 Da.

In forming the hydrophobic derivative of the natural biodegradable polysaccharide and as an example, a compound having a hydrocarbon segment can be covalently coupled to one or more portions of the polysaccharide. For example, the compound can be coupled to monomeric units along the length of the polysaccharide. This provides a polysaccharide derivative with one or more pendent groups. Each chemical group comprises a hydrocarbon segment. The hydrocarbon segment can constitute all of the pendent chemical group, or the hydrocarbon segment can constitute a portion of the pendent chemical group. For example, a portion of the hydrophobic polysaccharide can have the following structure, wherein M is a monomeric unit of the polysaccharide, and in the pendent chemical group ([L]-[H]), H is the hydrocarbon segment, and L is a chemical group linking the hydrocarbon segment to the monomeric unit of the polysaccharide:

[M]-[L]-[H] 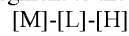

The pendent group can also include an additional portion that is not a hydrocarbon segment [N] as represented by the following structure:

[M]-[L]-[H]-[N] 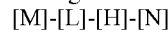

A "hydrocarbon segment" herein refers to a group of covalently bonded carbon atoms having the formula $(CH_n)_m$, wherein m is 2 or greater, and n is independently 2 or 1. A hydrocarbon segment can include saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups.

The monomeric units of the hydrophobic polysaccharides described herein typically include monomeric units having ring structures with one or more reactive groups. These reactive groups are exemplified by hydroxyl groups, such as the ones that are present on glucopyranose-based monomeric units of amylose and maltodextrin. These hydroxyl groups can be reacted with a compound that includes a hydrocarbon segment and a group that is reactive with the hydroxyl group (a hydroxyl-reactive group).

Examples of hydroxyl reactive groups include acetal, carboxyl, anhydride, acid halide, and the like. These groups can be used to form a hydrolytically cleavable covalent bond between the hydrocarbon segment and the polysaccharide backbone. For example, the method can provide a pendent group having a hydrocarbon segment, the pendent group linked to the polysaccharide backbone with a cleavable ester bond. In these aspects, the synthesized hydrophobic derivative of the natural biodegradable polysaccharide will include chemical linkages that are both enzymatically cleavable (the polymer backbone) and non-enzymatically hydrolytically cleavable (the linkage between the pendent group and the polymer backbone).

Other cleavable chemical linkages that can be used to bond the pendent groups to the polysaccharide include peroxyester groups, disulfide groups, and hydrazone groups.

In some cases the hydroxyl reactive groups include those such as isocyanate and epoxy. These groups can be used to form a non-cleavable covalent bond between the pendent group and the polysaccharide backbone. In these aspects, the synthesized hydrophobic derivative of the natural biodegradable polysaccharide includes chemical linkages that are enzymatically cleavable (the polymer backbone).

Other reactive groups, such as carboxyl groups, acetyl groups, or sulphate groups, are present on the ring structure of monomeric units of other natural biodegradable polysaccharides, such as chondrotin or hyaluronic acid. These groups can also be targeted for reaction with a compound having a hydrocarbon segment to be bonded to the polysaccharide backbone.

Various factors can be taken into consideration in the synthesis of the hydrophobic derivative of the natural biodegradable polysaccharide. These factors include the physical and chemical properties of the natural biodegradable polysaccharide, including its size, and the number and presence of reactive groups on the polysaccharide and solubility, the physical and chemical properties of the compound that includes the hydrocarbon segment, including its the size and solubility, and the reactivity of the compound with the polysaccharide.

In preparing the hydrophobic derivative of the natural biodegradable polysaccharide any suitable synthesis procedure can be performed. Synthesis can be carried out to provide a desired number of groups with hydrocarbon segments pendent from the polysaccharide backbone. The number and/or density of the pendent groups can be controlled, for example, by controlling the relative concentration of the compound that includes the hydrocarbon segment to the available reactive groups (e.g., hydroxyl groups) on the polysaccharide.

The type and amount of groups having the hydrocarbon segment pendent from the polysaccharide is sufficient for the hydrophobic polysaccharide to be insoluble in water. In order to achieve this, as a general approach, a hydrophobic polysaccharide is obtained or prepared wherein the groups having the hydrocarbon segment pendent from the polysaccharide backbone in an amount in the range of 0.25 (pendent group):1 (polysaccharide monomer) by weight.

To exemplify these levels of derivation, very low molecular weight (less than 10,000 Da) glucopyranose polymers are reacted with compounds having the hydrocarbon segment to provide low molecular weight hydrophobic glucopyranose polymers. In one mode of practice, the natural biodegradable polysaccharide maltodextrin in an amount of 10 g (MW 3000-5000 Da; ~3 mmols) is dissolved in a suitable solvent, such as tetrahydrofuran. Next, a solution having butyric anhydride in an amount of 18 g (0.11 mols) is added to the maltodextrin solution. The reaction is allowed to proceed, effectively forming pendent butyrate groups on the pyranose rings of the maltodextrin polymer. This level of derivation results in a degree of substitution (DS) of butyrate group of the hydroxyl groups on the maltodextrin of about 1.

For maltodextrin and other polysaccharides that include three hydroxyl groups per monomeric unit, on average, one of the three hydroxyl groups per glucopyranose monomeric unit becomes substituted with a butyrate group. A maltodextrin polymer having this level of substitution is referred to herein as maltodextrin-butyrate DS1. As described herein, the DS refers to the average number of reactive groups (including hydroxyl and other reactive groups) per monomeric unit that are substituted with groups comprising a hydrocarbon segment.

An increase in the DS can be achieved by incrementally increasing the amount of compound that provides the hydrocarbon segment to the polysaccharide. As another example, butyrylated maltodextrin having a DS of 2.5 is prepared by reacting 10 g of maltodextrin (MW 3000-5000 Da; ~3 mmols) with 0.32 mols butyric anhydride.

In some modes of practice, the invention provides an implant comprising hydrophobic glucopyranose polymer comprising a DS in the range of about 2-3, comprising pendent linear, branched, or cyclic a $C_4$-$C_{10}$ groups, and the polymer has a MW in the range of about 2000 to about 20000 Da.

In some modes of practice, the invention provides an implant comprising hydrophobic glucopyranose polymer comprising a DS in the range of about 2-3, comprising pendent linear, branched, or cyclic $C_5$-$C_7$ groups, and the polymer has a MW in the range of about 2000 to about 20000 Da The degree of substitution can influence the hydrophobic character of the polysaccharide. In turn, matrices formed from hydrophobic derivatives having a substantial amount of groups having the hydrocarbon segments bonded to the polysaccharide backbone (as exemplified by a high DS) are generally more hydrophobic and can be more resistant to degradation. For example, a matrix formed from maltodextrin-butyrate DS1 has a rate of degradation that is faster than a matrix formed from maltodextrin-butyrate DS2.

For polysaccharides having hydrolytically cleavable groups, penetration by an aqueous solution can promote hydrolysis and loss of the groups from the polysaccharide backbone. This can alter the properties of the implant, and can result in greater access to enzymes that promote the degradation of the natural biodegradable polysaccharide, and/or can result in the loss of the polysaccharides from the surface of the implant as they become solubilized.

Various synthetic schemes can be used for the preparation of a hydrophobic derivative of a natural biodegradable polysaccharide. In some modes of preparation, pendent polysaccharide hydroxyl groups are reacted with a compound that includes a hydrocarbon segment and a group that is reactive with the hydroxyl groups. This reaction can provide polysaccharide with pendent groups comprising hydrocarbon segments.

Any suitable chemical group can be coupled to the polysaccharide backbone and provide the polysaccharide with hydrophobic properties, wherein the polysaccharide becomes insoluble in water. Preferably, the pendent group includes one or more atoms selected from C, H, O, N, and S.

In some aspects, the pendent group comprises a hydrocarbon segment that is a linear, branched, or cyclic $C_2$-$C_{18}$ group. More preferably the hydrocarbon segment comprises a $C_2$-$C_{10}$, or a $C_4$-$C_8$, linear, branched, or cyclic group. The hydrocarbon segment can be saturated or unsaturated, and can comprise alkyl groups or aromatic groups, respectively. The hydrocarbon segment can be linked to the polysaccharide chain via a hydrolyzable bond or a non-hydrolyzable bond.

In some aspects the compound having a hydrocarbon segment that is reacted with the polysaccharide backbone is derived from a natural compound. Natural compounds with hydrocarbon segments include fatty acids, fats, oils, waxes, phospholipids, prostaglandins, thromboxanes, leukotrienes, terpenes, steroids, and lipid soluble vitamins.

Exemplary natural compounds with hydrocarbon segments include fatty acids and derivatives thereof, such as fatty acid anhydrides and fatty acid halides. Exemplary fatty acids and anhydrides include acetic, propionic, butyric, isobutyric, valeric, caproic, caprylic, capric, and lauric acids and anhydrides, respectively. The hydroxyl group of a polysaccharide can be reacted with a fatty acid or anhydride to bond the hydrocarbon segment of the compound to the polysaccharide via an ester group.

The hydroxyl group of a polysaccharide can also cause the ring opening of lactones to provide pendent open-chain hydroxy esters. Exemplary lactones that can be reacted with the polysaccharide include caprolactone and glycolides.

Generally, if compounds having large hydrocarbon segments are used for the synthesis of the hydrophobic derivative, a smaller amount of the compound may be needed for its synthesis. For example, as a general rule, if a compound having a hydrocarbon segments with an alkyl chain length of $C_x$ is used to prepare a hydrophobic derivative with a DS of 1, a compound having a hydrocarbon segment with an alkyl chain length of $C_{(x \times 2)}$ is reacted in an amount to provide a hydrophobic derivative with a DS of 0.5.

The hydrophobic derivative of the natural biodegradable polysaccharide can also be synthesized having combinations of pendent groups with two or more different hydrocarbon segments, respectively. For example, the hydrophobic derivative can be synthesized using compounds having hydrocarbon segments with different alkyl chain lengths. In one mode of practice, a polysaccharide is reacted with a mixture of two or more fatty acids (or derivatives thereof) selected from the group of acetic acid, propionic acid, butyric acid, isobutyric acid, valeric acid, caproic acid, caprylic acid, capric acid, and lauric acid to generate the hydrophobic derivative.

In other cases the hydrophobic derivative is synthesized having a non-hydrolyzable bond linking the hydrocarbon segment to the polysaccharide backbone. Exemplary non-hydrolyzable bonds include urethane bonds.

The hydrophobic derivative of the natural biodegradable polysaccharide can also be synthesized so that hydrocarbon segments are individually linked to the polysaccharide backbone via both hydrolyzable and non-hydrolyzable bonds. As another example, a hydrophobic derivative is prepared by reacting a mixture of butyric acid anhydride and butyl isocyanate with maltodextrin. This yields a hydrophobic derivative of maltodextrin with pendent butyric acid groups that are individually covalently bonded to the maltodextrin backbone with hydrolyzable ester linkages and non-hydrolyzable urethane linkages. The degradation of an article having this type of hydrophobic derivative can occur by loss of the butyrate groups from hydrolysis of the ester linkages. However, a portion of the butyrate groups (the ones that are bonded via the urethane groups) are not removed from the polysaccharide backbone and therefore the natural biodegradable polysaccharide can maintain a desired degree of hydrophobicity, prior to enzymatic degradation of the polysaccharide backbone.

In some aspects, the group that is pendent from the polysaccharide backbone has properties of a bioactive agent. In this regard, the implant comprises polysaccharide-coupled bioactive agent. In some aspects, a bioactive agent which has a hydrocarbon segment can be hydrolyzed from the natural biodegradable polymer and released from the matrix to provide a therapeutic effect. One example of a therapeutically useful compound having a hydrocarbon segments is butyric acid, which has been shown to elicit tumor cell differentiation and apoptosis, and is thought to be useful for the treatment of cancer and other blood diseases.

Other illustrative compounds comprising hydrocarbon segments include valproic acid and retinoic acid. These compounds can be coupled to a polysaccharide backbone to provide a pendent group, and then cleaved from the polysaccharide backbone following implantation of the article in a subject. Retinoic acid is known to possess antiproliferative effects and is thought to be useful for treatment of proliferative vitreoretinopathy (PVR). The pendent group that provides a therapeutic effect can also be a natural compound (such as butyric acid, valproic acid, and retinoic acid).

Other illustrative compound that can be coupled to the polysaccharide backbone is a corticosteroid. An exemplary corticosteroid is triamcinolone. One method of coupling triamcinolone to a natural biodegradable polymer is by employing a modification of the method described in Cayanis, E. et al., *Generation of an Auto-anti-idiotypic Antibody that Binds to Glucocorticoid Receptor*, The Journal of Biol. Chem., 261(11): 5094-5103 (1986). Triamcinolone hexanoic acid is prepared by reaction of triamcinolone with ketohexanoic acid; an acid chloride of the resulting triamcinolone hexanoic acid can be formed and then reacted with the natural biodegradable polymer, such as maltodextrin or polyalditol, resulting in pendent triamcinolone groups coupled via ester bonds to the natural biodegradable polymer.

The hydrophobic derivative of the natural biodegradable polysaccharide can also be synthesized having two or more different pendent groups, wherein at least one of the pendent groups comprises a bioactive agent. The hydrophobic polysaccharide can be synthesized with an amount of a pendent groups comprising a bioactive agent, that when released from the polysaccharide, provides a therapeutic effect to the subject. An example of such a hydrophobic derivative is maltodextrin-caproate-triamcinolone. This hydrophobic derivative can be prepared by reacting a mixture including triamcinolone hexanoic acid and an excess of caproic anhydride (n-hexanoic anhydride) with maltodextrin to provide a derivative with a DS of 2.5.

In some aspects, the group that is pendent from the polysaccharide includes a hydrocarbon segment that is an aromatic group, such as a phenyl group. As one example, o-acetylsalicylic acid is reacted with a polysaccharide such as maltodextrin to provide pendent chemical group having a hydrocarbon segment that is a phenyl group, and a non-hydrocarbon segment that is an acetate group wherein the pendent group is linked to the polysaccharide via an ester bond.

The term "bioactive agent," refers to an inorganic or organic molecule, which can be synthetic or natural, that causes a biological effect when administered in vivo to a subject. The invention contemplates implants having bioactive agent within the matrix, but not coupled to the hydrophobic polysaccharide, bioactive agent coupled to the hydrophobic polysaccharide, and combinations thereof.

A partial list of bioactive agents is provided below. According to embodiments of the present invention, one may choose one or more of the bioactive agents to be included in an implant formed of the hydrophobic derivative of the natural biodegradable polysaccharide. A comprehensive listing of bioactive agents, in addition to information of the water solubility of the bioactive agents, can be found in *The Merck Index*, Thirteenth Edition, Merck & Co. (2001).

Implants prepared according to the invention can be used to release bioactive agents falling within one or more of the following classes include, but are not limited to: ACE inhibitors, actin inhibitors, analgesics, anesthetics, anti-hypertensives, anti polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

Antibiotics are art recognized and are substances which inhibit the growth of or kill microorganisms. Examples of antibiotics include penicillin, tetracycline, chloramphenicol, minocycline, doxycycline, vancomycin, bacitracin, kanamycin, neomycin, gentamycin, erythromycin, cephalosporins, geldanamycin, and analogs thereof. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Anti-viral agents are substances capable of destroying or suppressing the replication of viruses. Examples of anti-viral agents include $\alpha$-methyl-P-adamantane methylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCl, tacrine, 1-hydroxymaleate, iodotubercidin, p-bromotetramisole, 10-($\alpha$-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(−), deprenyl HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthine, papaverine HCl, indomethacin, 2-cyclooctyl-2-hydroxyethylamine hydrochloride, 2,3-dichloro-$\alpha$-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−) alpha-methyltyrosine, D L(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances that have an anesthetic effect in a localized region. Examples of such anesthetics include procaine, lidocaine, tetracaine and dibucaine.

Examples of statins include lovastatin, pravastatin, simvastatin, fluvastatin, atorvastatin, cerivastatin, rosuvastatin, and superstatin.

Examples of steroids include glucocorticoids such as cortisone, hydrocortisone, dexamethasone, betamethasone, prednisone, prednisolone, methylprednisolone, triamcinolone, beclomethasone, fludrocortisone, and aldosterone; sex steroids such as testosterone, dihydrotestosterone, estradiol, diethylstilbestrol, progesterone, and progestins.

The bioactive agent can be an immunosuppressive agent, for example, rapamycin, ABT-578, cyclosporine, everolimus, mycophenolic acid, sirolimus, tacrolimus, and the like.

The implants of the present invention can be prepared by preparing a composition that includes the hydrophobic derivative of a natural biodegradable polysaccharide and one or more bioactive agent(s). In the composition, the bioactive agent can be in mixture with the hydrophobic derivative (but not coupled to the hydrophobic derivative), coupled to the hydrophobic derivative, or both.

To illustrate one method of preparing the implant, a composition is prepared by the addition of a bioactive agent to the hydrophobic derivative of the natural biodegradable polysaccharide. The bioactive agent and the hydrophobic derivative are placed in a vessel and heated together, which melts the hydrophobic derivative. The composition is then mixed to blend the bioactive agent into the melted hydrophobic derivative. The composition can then be shaped into a desired form.

In cases where high drug loading is desired, the natural biodegradable polysaccharide and the bioactive agent can, in combination, comprise about 90% or greater by weight, 95% or greater by weight, 97.5% or greater by weight, or 99% or greater by weight, of the total weight of the implant.

For example, in some aspects, bioactive agent is present in an amount in the range of about 10 wt % to about 65 wt % of the implant, and the hydrophobic derivative of the natural biodegradable polysaccharide is present in the rang of about 90 wt % to about 35 wt % of the implant. In more specific aspects, bioactive agent is present in an amount in the range of about 25 wt % to about 55 wt % of the implant, and the hydrophobic derivative is present in the range of about 75 wt % to about 45 wt % of the implant. In even more specific aspects, bioactive agent is present in an amount in the range of about 40 wt % to about 50 wt % of the implant, and the hydrophobic derivative is present in the range of about 60 wt % to about 50 wt % of the implant.

In forming a medical implant, use of higher concentrations of the natural biodegradable polysaccharide may provide a more structurally rigid and durable implant. This can be useful when the implant is subjected to harsh conditions during and/or after delivering the implant to a target location, and can reduce the risk of the implant fracturing.

In addition, use of higher concentrations of the natural biodegradable polysaccharide may provide implant with a slower rate of bioactive agent release.

In some preferred modes of practice the implant is made using a process that does not include any substantial amount of solvent. For example, the implant can be prepared using a solvent-less process, which is beneficial if it is desired to maintain the bioactive agent in a particular polymorphic form, or a non-polymorphic form throughout the process.

It is known that polymorphs of a bioactive agent have solid crystalline phases with different internal crystal lattices. For some bioactive agents, differences due to polymorphism and can affect bioavailability and effective clinical use, while in other cases, differences in polymorphism have little effect on bioactivity. With this in mind, it is generally desirable to maintain the bioactive agent in its original polymorphic form during the process of forming the implant, particularly if the bioactivity of a bioactive agent in a certain polymorphic form is understood, or importantly approved for use in the body.

A medical implant having a defined structure can be formed by any suitable process, including molding, extruding, shaping, cutting, casting, and the like, or combinations of these processes. In forming a medical implant, the concentration of the natural biodegradable polysaccharide may be higher to provide a more structurally rigid implant.

In one mode of practice, the implants of the present invention are formed using an extruder. Materials used to form an implant including the hydrophobic derivative of the natural biodegradable polysaccharide and bioactive agent, are first fed into the extruder in dry form. The extruder heats the materials, which causes melting of the hydrophobic derivative, which can then be mixed in the extruder to blend in the bioactive agent. The extruded can be heated to a temperature of about 80° C. or greater, or about 100° C. or greater to cause melting of the hydrophobic derivative. Higher temperatures (such as greater than 140° C.) may be used if a hydrophobic derivative having a higher Tg is used to form the implant. (In cases where the bioactive agent is only coupled to the polysaccharide, the blending step may be optional.) The ingredients can be mixed for a period of time, such as less than 10 minutes, before being extruded. After melting and mixing, the mixture can be extruded out of a die into a desired shape. Further shaping, such as cutting, can be performed after the extruded material cools to provide an implant in a final form. In some cases the implant has a diameter in the range of about 100 µm to about 1000 µm, and in more specific aspects about 250 µm to about 650 µm.

The process of forming the implant can be performed as a continuous process or a batch process. For example, the process can include continuous extrusion to form the mixture and shape the device, batch extrusion to form the mixture and shape the device, or continuous extrusion to form the mixture followed by molding to form the device.

The process of the present invention can be used to form an implant having a more complex shape. These more complex shapes can include multiple deviations from a linear path, such as in coil or helically-shaped implants. Other contemplated shapes are semi-circular or "half ring" shapes. In some cases the more complex shape can be formed by an extrusion or molding process. For example, extrusion may be used to form a coil by winding a cylindrical extrudate as it cools. Molding can also be used to form a coil. Add claim for helical or coil shape.

In some aspects the implant comprises a biocompatible hydrophilic polymer. The biocompatible hydrophilic polysaccharide can increase the rate of release of the bioactive agent from the matrix, as compared to an equivalent matrix that does not include the biocompatible hydrophilic polymer. The biocompatible hydrophilic polymer can be biodegradable or non-biodegradable. Exemplary biocompatible hydrophilic polymers include poly(ethylene glycol), hydrophilic polysaccharides, polyvinyl pyrrolidones, polyvinyl alcohols, low molecular weight methyl cellulose, hydroxypropyl methyl cellulose (HPMC), and the like.

The biodegradable hydrophilic polymer is thought to create hydrophilic domains in the hydrophobic matrix. The hydrophilic domains are thought to drive fluid into the matrix after the implant has been placed within a subject. In one proposed mechanism, release of the bioactive agent is thought to be promoted by an increase in osmotic pressure with the matrix, which forces bioactive agent out of the matrix. In another proposed mechanism, release of the bioactive agent is thought to be promoted by the hydrolysis of pendent groups that include the hydrocarbon segments that are linked via hydrolytically cleavable ester groups. This decreases the hydrophobicity of the matrix, and increases the rate of release of the bioactive agent.

For example, in some aspects, bioactive agent is present in an amount in the range of about 10 wt % to about 65 wt % of the implant, and the hydrophobic derivative of the natural biodegradable polysaccharide is present in the range of about 70 wt % to about 35 wt % of the implant, and the biodegradable hydrophilic polymer is present in the implant in an amount in the range of about 1 wt % to about 20 wt %.

In more specific aspects, bioactive agent is present in an amount in the range of about 25 wt % to about 55 wt % of the implant, the hydrophobic derivative is present in the range of about 60 wt % to about 40 wt % of the implant, and the biodegradable hydrophilic polymer is present in the implant in an amount in the range of about 5 wt % to about 15 wt %.

In even more specific aspects, bioactive agent is present in an amount in the range of about 40 wt % to about 50 wt % of the implant, the hydrophobic derivative is present in the range of about 50 wt % to about 40 wt % of the implant, and the biodegradable hydrophilic polymer is present in the implant in an amount in the range of about 7.5 wt % to about 12.5 wt %.

Optionally, the implant can be prepared using a solvent. For example, solvent-based procedures can be used if the bioactive agent is otherwise unstable at temperatures that melt the hydrophobic derivative of the natural biodegradable polysaccharide. Examples of solvents that can be used in a composition to prepare the implant include aromatic compounds such as toluene and xylene, and ethers such as tetrahydrofuran. Other suitable solvents include halogenated alkanes such as methylene chloride and chloroform; and amides such as dimethylfoiuiamide (DMF). Combinations of one or more of these or other solvents can also be used. The type of solvent system used can be chosen according to the hydrophobic derivative, and any other optional component present in the composition.

The hydrophobic derivative can optionally be blended with one or more other hydrophobic compounds in a composition for preparation of the implant. The other hydrophobic compounds can be biodegradable polymers. For example, the implant can be prepared using a blend of two or more different hydrophobic derivatives of natural biodegradable polysaccharides. The hydrophobic derivatives can differ with regards to one or more of the following aspects: molecular weight, and type and amount of groups pendent from the polysaccharide backbone.

The hydrophobic derivative can also be blended with different types of biodegradable polymers. Examples include polyesters such as poly(lactic acid) (poly(lactide)), poly(glycolic acid) (poly(glycolide)) poly(lactide-co-glycolide), poly (dioxanone); polylactones such as poly(caprolactone) and poly(valerolactone), copolymers such as poly(glycolide-co-polydioxanone), poly(glycolide-co-trimethylene carbonate), and poly(glycolide-co-caprolactone); poly(3-hydroxybutyrate), poly(3-hydroxyvalerate), poly(tartronic acid), poly (β-malonic acid), poly(propylene fumarate); degradable polyesteramides; degradable polyanhydrides and polyalkeneanhydrides (such as poly(sebacic acid), poly(1,6-bis(carboxyphenoxy)hexane, poly(1,3-bis(carboxyphenoxy)propane); degradable polycarbonates and aliphatic carbonates; degradable polyiminocarbonates; degradable polyarylates; degradable polyorthoesters; degradable polyurethanes; degradable polyphosphazenes; degradable polyhydroxyalkanoates; degradable polyamides; degradable polypeptides; and copolymers thereof.

Other optional components can be included in the implant. These components can be included in amounts less than the amounts of polysaccharide or bioactive agent in the implant. These optional components can change or improve the properties of the implant.

Components that can facilitate the detection of the implant include colorants, radiopacifying agents, and radioisotopes. The presence of one or more of these components can facilitate detection of the location of implant following implantation.

Another class of optional components is excipients. Excipients can improve the stability of the bioactive agent that is associated with the implant and/or act as a plasticizing agent to change the physical property of the implant. Exemplary excipients include glycerol, diethylene glycol, sorbitol, sorbitol esters, maltitol, sucrose, fructose, invert sugars, corn syrup, and mixtures thereof. The amount and type of excipient(s) can be based on known standards and techniques. Antioxidants can be added to the implant to maintain implant properties, including the stability of the bioactive agent.

Optional components can also be used to change the elasticity, flexibility, wettability, or adherent properties, (or combinations thereof) of the implant.

Optionally, an implant can include a coating formed on all or a portion of its surface. If a coating is present, it is also preferably of a compound that can be dissolved or degraded following implantation of the article. For example, the coating can include a biodegradable polymer which can be the same or different than the hydrophobic derivative that is used to form the bulk of the implant. A coating may be applied to the implant to delay or hinder the initial release of the bioactive agent from the implantable article. A lubricious coating can may also be formed on the implant to facilitate its delivery to a target site by reducing frictional forces that may be associated with its delivery.

An exemplary spray coating process and apparatus that can be used for coating implants of the present invention is described in U.S. Patent Publication No. 2004-0062875-A1 (filed Sep. 27, 2002).

Implants formed from the hydrophobic derivative, or that include a biodegradable coating can be treated to sterilize one or more parts of the article, or the entire implant. Sterilization can take place prior to using the implant and/or, in some cases, during implantation of the medical article. For example, the ocular implant can be sterilized before insertion into the eye. In some aspects the ocular implant can be contacted with an aqueous sterilization solution.

To illustrate aspects of the invention, the hydrophobic derivative is utilized to form an ophthalmic article, such as an ocular implant. The ocular implant can be configured for placement at a desired portion of the eye. For example, the implants of the present invention are particularly suitable for placement at internal target locations in the eye and for release of the bioactive agent at that location. In some aspects, the ocular implant is utilized to deliver bioactive agent to a posterior segment of the eye (behind the lens).

In some aspects, the ocular implant can be configured for placement at a subretinal area within the eye. In some aspects the ocular implant is used in association with an ophthalmic device. Ophthalmic devices are described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. application Ser. No. 11/175,850 ("Methods and Devices for the Treatment of Ocular Conditions," de Juan et al.); and related applications.

The ocular implants are typically designed to minimize interference with the functions of the eye, and discomfort and damage to the eye. In some embodiments, the implant is rod-like or filament-like in shape. In some embodiments, the implant may have a distal end that is beveled, tapered, or sharpened. Alternatively, the implant may have a distal end that is blunt or rounded.

In some embodiments, the implant has a total diameter that is no greater than about 1000 µm, in other embodiments no greater than about 900 µm, in other embodiments no greater than about 800 µm, in other embodiments no greater than about 700 µm, in other embodiments no greater than about 600 µm, in other embodiments no greater than about 500 µm, in other embodiments no greater than about 400 µm, in other embodiments no greater than about 300 µm, in other embodiments no greater than about 200 µm, in other embodiments no greater than about 100 µm, in other embodiments no greater than about 50 µm. In some embodiments, the total diameter of the implant ranges from about 200 µm to about 500 µm.

In some embodiments, the implants of the invention have a length that is no greater than about 5 mm, in other embodiments no greater than about 4.5 mm, in other embodiments no greater than about 4 mm, in other embodiments no greater than about 3.5 mm, in other embodiments no greater than about 3.0 mm, in other embodiments no greater than about 2.9 mm, in other embodiments no greater than about 2.8 mm, in other embodiments no greater than about 2.7 mm, in other embodiments no greater than about 2.6 mm, in other embodiments no greater than about 2.5 mm, in other embodiments no greater than about 2.4 mm, in other embodiments no greater than about 2.3 mm, in other embodiments no greater than about 2.2 mm, in, other embodiments no greater than about 2.1 mm, in other embodiments no greater than about 2 mm. In some embodiments, the length of the implant ranges from about 2.25 mm to about 2.75 mm.

In some aspects of the invention the natural biodegradable polymer is used to form the body member of an ocular implant, wherein the body member has a dry weight of about 6 mg or less. In some aspects the body member has a dry weight of about 2.5 mg or less. In some aspects the body member has a dry weight of about 2.3 mg or less. In some aspects the body member has a dry weight of about 2.0 mg or less. In some aspects the body member has a dry weight of about 1.8 mg or less. In some aspects the body member has a dry weight of about 1.5 mg or less.

According to the invention, bioactive agent is made available to a subject using a method that involves the following steps. One step is implanting at a target site in a subject a biodegradable medical implant comprising a matrix of hydrophobic natural biodegradable polysaccharides and bioactive-agent within the matrix. Another step is allowing the bioactive agent to be released from the implant in the subject following the step of implanting.

While the step of implanting can be performed to place the implant at a desired location anywhere in the body, the process is exemplified by placement of an ocular implant at an ocular location.

An ocular implant formed of hydrophobic derivatives of natural biodegradable polysaccharides can be implanted into a portion of the eye using any suitable method. Typically, the implant is delivered using an insertion instrument to provide the implant to the targeted site within the eye. The term "implantation site" refers to the site within a patient's body at which the implant is located during a treatment course according to the invention.

The ocular implant can be placed at an implantation site within the eye tissues. Suitable ocular implants can perform a function and/or provide bioactive agent to any desired area of the eye. For example, an implantation site can be chosen to provide bioactive agent primarily to an anterior segment of the eye (in front of the lens), or to a posterior segment of the eye (behind the lens). Suitable ocular implants can also be utilized to provide bioactive agent to tissues in proximity to the eye, when desired. In some aspects, the ophthalmic article can be configured for placement at an intraocular site, such as the vitreous or subretinal space.

The vitreous chamber is the largest chamber of the eye and contains the vitreous humor or vitreous. Generally speaking, the vitreous is bound interiorly by the lens, posterior lens zonules and ciliary body, and posteriorly by the retinal cup. The vitreous is a transparent, viscoelastic gel that is 98% water and has a viscosity of about 2-4 times that of water. The main constituents of the vitreous are hyaluronic acid (HA) molecules and type II collagen fibers, which entrap the HA molecules. The viscosity is typically dependent on the concentration of HA within the vitreous. The vitreous is traditionally regarded as consisting of two portions: a cortical zone, characterized by more densely arranged collagen fibrils, and a more liquid central vitreous.

Therefore, in some aspects, the invention provides methods for placing an ocular implant at a site within the body, the site comprising a gel-like material, such as viscoelastic gel.

In many aspects of the invention, the ocular implant is placed in the vitreous. In some aspects, the ocular implant can be delivered through the scleral tissue (trans-scleral injection). Typically, intravitreal delivery will be accomplished by using an insertion instrument utilizing a 25 to 30-gauge needle (or smaller gauge) having a length of about 0.5 inches to about 0.62 inches.

This methodology also yields a technique that can be implemented in an outpatient clinic setting. According to this embodiment, a insertion instrument or device is provided (e.g., a cannula or syringe), a portion of which is configured and arranged such that when the instrument is inserted into the eye, the opening formed in the sclera to receive the instrument is small enough so as to not require sutures to seal or close the opening in the sclera. In other words, the opening is small enough that the wound or opening is self-sealing, thereby preventing the vitreous humor from leaking out of the eye.

In addition, the step of inserting can further include inserting the insertable portion of the insertion instrument or device transconjunctivally so the operable end thereof is within the vitreous. In this regard, transconjunctival shall be understood to mean that the instrument's operable end is inserted through both the conjunctiva and through the sclera into the vitreous. More particularly, inserting the insertable portion that forms an opening in the sclera and the conjunctiva that is small enough so as to not require sutures or the like to seal or close the opening in the sclera. In conventional surgical techniques for the posterior segment of the eye, the conjunctiva is routinely dissected to expose the sclera, whereas according to the methodology of this embodiment, the conjunctiva need not be dissected or pulled back.

Consequently, when the instrument is removed from the eye, the surgeon does not have to seal or close the opening in the sclera with sutures to prevent leaking of the aqueous humor, since such an opening or wound in the sclera is self-sealing. In addition, with the transconjunctival approach, the surgeon does not have to reattach the dissected conjunctiva. These features can further simplify the surgical procedure, as well as reduce (if not eliminate) suturing required under the surgical procedure.

It will be understood that the inventive methods do not require dissection of the conjunctiva. However, if such additional step is desired in a particular treatment, such conjunctival dissection could be performed.

The insertion procedure can be performed without vitrectomy and results in a self-sealing sclerotomy, eliminating the need for sutures and minimizing risk of infection. In some aspects, the small sclerotomy is leakage-free, thereby reducing risk of leakage of vitreous from the implantation site. Advantageously, the inventive methods can be performed as an office-based procedure.

In some aspects, the ocular implant in placed at a subretinal area within the eye. An insertion instrument can be advanced transconjunctively and trans-retinally, to reach the subretinal space within the eye to deliver the implant. Once the tip of the instrument has reached the subretinal space, a limited or localized retinal detachment (e.g., a bleb detachment) can be formed using any of a number of devices and/or techniques known to those skilled in the art, thereby defining or forming a subretinal space. The implant can then be placed in the subretinal space formed by the retinal detachment. The limited or local dome-shaped subretinal detachment is created in such a fashion that the detachment itself generally does not have an appreciable or noticeable long-term effect on the vision of the patient.

In some cases, a grasping member (such as forceps) can be used to locate (for example, by pulling) the ocular implant at the desired implantation site. The ocular implant can then reside at the implantation site during a treatment course.

At the target site, the implants of the present invention release bioactive agent that is intended to treat a medical condition. For ocular implants, the medical condition treated is generally associated with one or more of three types of indications: (1) angiogenesis, (2) inflammation, and (3) degeneration. Depending on the condition(s) and the severity of the condition, one or more bioactive agent suitable for treatment of the condition is included in the implant and released at the target location for treatment. The bioactive agent can be any one capable of being released from the implant for the treatment of a condition, including those listed herein.

The implant can be used for the treatment of diabetic retinopathy, which is characterized by angiogenesis in the retinal tissue.

Diabetic retinopathy has four stages. While the implant can be delivered to a subject diagnosed with diabetic retinopathy during any of these four stages, it is common to treat the condition at a later stage.

The first stage is mild nonproliferative retinopathy which is characterized by the appearance of microaneurysms in retinal blood vessels. The second stage is moderate nonproliferative retinopathy which is characterized by blockage of the retinal blood vessels. The third stage is severe nonproliferative retinopathy which is characterized by a more extensive blockage of the retinal blood vessels, which deprive several areas of the retina with their blood supply and results in the formation of new blood vessels in the retina (angiogenesis) in response to this deprivation. The fourth stage is proliferative retinopathy which is characterized by active formation of new blood vessels, which have an abnormal morphology. These abnormally-formed vessels grow along the retinal and vitreal surface and are prone to leak blood, which can result in severe vision loss.

The treatment of diabetic retinopathy can be accomplished by delivering the implant to a target location so that one or more anti-angiogenic factors is released from the implant and affects sub-retinal tissue. In some aspects the bioactive agent is an inhibitor of angiogenesis such as anecortave acetate, or a receptor tyrosine kinase antagonist.

Compounds and methods for treating diabetic retinopathy with a receptor tyrosine kinase antagonist have been described in U.S. Pat. No. 5,919,813. In some aspects, the implant of the present invention comprises a compound of formula I:

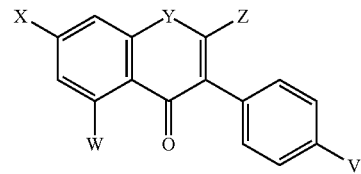

wherein V, W and X are selected from the group consisting of hydro, hydroxyl, alkoxy, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl. In some aspects, the alkoxy is a C$_1$-C$_6$ alkoxy. In some aspects, the halo is fluorine, chlorine or bromine. In some aspects, the ester is a C$_1$-C$_6$ ester. In some aspects, the ether is a C$_1$-C$_6$ ether. Pharmaceutically acceptable salts of the carboxylic acid group include sodium and potassium salts. In some aspects, the alkyl groups are C$_1$-C$_6$ alkyl groups. In some aspects, the protein tyrosine kinase pathway inhibitor is genistein.

Exemplary dosage ranges using a compound of formula I are from about 1 mg/kg/day to about 100 mg/kg/day, or more specifically from about 15 mg/kg/day to about 50 mg/kg/day.

Combination drug delivery strategies can also be carried out for the treatment of diabetic retinopathy. For example, retinal tissue can be treated with one or more neurotrophic factors. Exemplary neurotrophic factors include ciliary neurotrophic factor (CNTF) and glial cell-derived neurotrophic factor (GDNF). In addition neuroprotective agents such as coenzyme Q10, creatine, and minocycline can be delivered from the implant. As an example, minocycline is thought to be a neuroprotective agent (in addition to its role as an antibiotic with anti-inflammatory effects) as it may also prevent the cascade of events leading to programmed cell death (apoptosis).

The treatment of diabetic retinopathy can be performed by administration of the implant alone, or can be performed with other procedures such as laser surgery and/or vitrectomy.

The implant can be used for the treatment of uveitis, which is characterized by inflammation of the uvea. The uvea is the layer of the eye between the sclera and the retina and includes the iris, ciliary body, and choroid. The uvea provides most of the blood supply to the retina.

Forms of uveitis include anterior uveitis, which typically involves inflammation that is limited to the iris (iritis). Another form of uveitis involves inflammation of the pars plana (between the iris and the choroid). Another form of uveitis is posterior uveitis affects primarily the choroid (choroiditis). The implant of the present invention can be delivered to a target site in the eye for the treatment of any of these particular conditions.

The present invention contemplates treating uveitis by instilling or disposing one or more anti-inflammatory factors in the sub-retinal space.

In a more particular aspect of the present invention, steroids, including anti-inflammatory steroids and corticosteroids, are disposed or instilled in the sub-retinal space. Exemplary anti-inflammatory steroids and corticosteroids include hydrocortisone, hydrocortisone acetate, dexamethasone 21-phosphate, fluocinolone, medrysone, methylprednisolone, prednisolone 21-phosphate, prednisolone acetate, fluorometхалone, betamethasone, and triamcinolone, or triamcinolone acetonide.

In an exemplary embodiment, the dosage of the steroid is between about 10 μg and about 500 μg over a period of time in the range of about three to about twelve months. This dosage range is applicable to each of the three following stages of macular degeneration, namely: early onset macular degeneration, atrophic macular degeneration (AMD) and neovascular macular degeneration (NMD).

The implant can also be used for the treatment of retinitis pigmentosa, which is characterized by retinal degeneration. For example, the present invention contemplates treating retinitis pigmentosa by instilling or disposing one or more neurotrophic factors in the sub-retinal space.

The implant can also be used for the treatment of age-related macular degeneration (AMD). AMD is characterized by both angiogenesis and retinal degeneration. Specific forms of AMD include, but are not limited to, dry age-related macular degeneration, exudative age-related macular degeneration, and myopic degeneration. The implant of the present invention can be delivered to a target site in the eye for the treatment of any of these forms of AMD. In some cases, an implant is delivered to the sub-retinal space for the treatment of AMD. As an example, the implant can be used to deliver one or more of the following drugs for the treatment of AMD: anti-VEGF (vascular endothelial growth factor) compounds, neurotrophic factors, and/or anti-angiogenic factors. In some specific aspects, the implant is used to release a corticosteriod for the treatment of sub-retinal tissue.

The implant can also be used for the treatment of glaucoma, which is characterized by increased ocular pressure and loss of retinal ganglion cells. The implant of the present invention can be delivered to a target site in the eye for the treatment of glaucoma contemplated for the release of one or more neuroprotective agents that protect cells from excitotoxic damage. Such agents include N-methyl-D-aspartate (NMDA) antagonists, cytokines, and neurotrophic factors.

An ocular condition can also be treated by delivering the implant to a target location in the eye to release an antiproliferative agent, such as 13-cis retinoic acid, retinoic acid derivatives, 5-fluorouracil, taxol, rapamycin, analogues of rapamycin, tacrolimus, ABT-578, everolimus, paclitaxel, taxane, or vinorelbine.

An ocular condition can also be treated by delivering the implant to a target location in the eye to release a beta adrenergic agent such as isoproterenol, epinephrine, norepinephrine (agonists) and propranolol (antagonist).

An ocular condition can also be treated by delivering the implant to a target location in the eye to release a prostaglandin such as $PGE_2$ or $PGF_2$.

The implant of the present invention can also be used for the prophylactic treatment of a subject. In other words, the implant may be provided to a subject even if there has not been a diagnosed existence of a disorder or disease. For example, in more than 50% of cases where AMD occurs in one eye, it will subsequently occur in the unaffected eye within a year. In such cases, prophylactic administration of a therapeutic medium such as a steroid into the unaffected eye may prove to be useful in minimizing the risk of, or preventing, AMD in the unaffected eye.

The bioactive agent can be released for a period of time and in an amount sufficient to treat a medical condition in a subject. As mentioned, one distinct advantage of the present invention are that bioactive agents can be released from the implant at a steady rate, meaning that there is not substantial variation in amount of bioactive agent released per day over the bioactive agent release period of the implant. Given this, the implants of the invention allow for drug delivery that is close to a zero-order release rate. The bioactive agent can also be released in therapeutically effective amounts for treatment of medical conditions.

In some aspects, the bioactive agent is released at an average rate in the range of 100 ng/day to 10 μg/day. In more specific aspects, the bioactive agent is released at an average rate in the range of 250 ng/day to 7.5 μg/day. In yet more specific aspects, the bioactive agent is released at an average rate in the range of 500 ng/day to 5 μg/day. In yet more specific aspects, the bioactive agent is released at an average rate in the range of 750 ng/day to 2.5 μg/day. In yet more specific aspects, the bioactive agent is released at an average rate of approximately 1 μg/day.

Another distinct advantage is that implants can be prepared having a particularly long bioactive agent release period, in which therapeutically effective amounts of bioactive agent are able to be released at later points during this period. With regard to bioactive agent release, the implant can have a "half-life," which is the period of time at which half of the total amount of bioactive agent that is present in the implant is released during the bioactive agent release period.

For example, in one aspect, 50% of the amount of bioactive agent present in the implant is released from the implant after a period of 100 days. In this regard, the implant can be used for the treatment of medical conditions wherein bioactive agent is to be released for a period of time of about 3 months or greater, a period of time of about 6 months or greater, a period of time of about 9 months or greater, a period of time of about 12 months or greater, a period of time in the range of about 3 to about 6 months, a period of time in the range of about 3 to about 9 months, a period of time in the range of about 3 to about 12 months, or a period of time in the range of about 3 to about 18 months.

In some cases, a biocompatible hydrophilic polymer can be included in the implant to fine-tune its in vivo functional life. In some aspects, 50% of the bioactive agent is released from the implant at a time point in the range of 10-70 days. In more specific aspects, 50% of the bioactive agent is released from the implant at a time point in the range of 15-40 days. In yet more specific aspects, 50% of the bioactive agent is released from the implant at a time point in the range of 20-35 days. In yet more specific aspects, 50% of the bioactive agent is released from the implant at a time point in the range of 25-30 days.

In some aspects, depending on the properties of the implant, a carbohydrase can promote the degradation of the implant. For example, the groups comprising the hydrocarbon segments and which are pendent from the polysaccharide backbone can be released from the polysaccharide by hydrolytic cleavage, and a portion of the implant can become accessible to a carbohydrase, which can enzymatically digest the polysaccharide and degrade the implant.

In these aspects, hydrolysis of the ester bond, which can occur non-enzymatically, and enzymatic hydrolysis of the linkages between the monomeric (or dimeric) units of the polysaccharide portion can contribute to degradation of the article. For example, non-enzymatic hydrolysis can lead to cleavage and loss of the groups that include the hydrocarbon segment, from the polysaccharide backbone. This loss may lead to a portion of the article becoming more hydrophilic, and subject to attack by a carbohydrase resulting in biodegradation of the polysaccharide, and/or further decomposition of the article by loss of the polysaccharide from the surface.

Degradation by a carbohydrase may occur before, during, or/and after the release of the bioactive agent. Examples of carbohydrases that can specifically degrade natural biodegradable polysaccharide include α-amylases, such as salivary and pancreatic α-amylases; disaccharidases, such as maltase, lactase and sucrase; trisaccharidases; and glucoamylase (amyloglucosidase).

Serum concentrations for amylase are estimated to be in the range of about 50-100 U per liter, and vitreal concentrations also fall within this range (Varela, R. A., and Bossart, G. D. (2005) *J Am Vet Med Assoc* 226:88-92).

In some aspects, a carbohydrase can be administered to a subject to increase its concentration in the body fluid or tissue surrounding the implant, so that the carbohydrase may promote the degradation of the implant. Exemplary routes for introducing a carbohydrase include local injection, intravenous (IV) routes, and the like. Alternatively, degradation can be promoted by indirectly increasing the concentration of a carbohydrase in the vicinity of the implant, for example, by a dietary process, or by ingesting or administering a compound that increases the systemic levels of a carbohydrase.

In other cases, the carbohydrase can be provided on a portion of the implant. For example the carbohydrase may be released from a portion of the implant to promote its own degradation.

The coating can also be eroded by liberation of polysaccharides from the surface of the implant. For example, after pendent groups are released from the polysaccharide by hydrolytic cleavage, the polysaccharide can loose its hydrophobic association with the remaining portion of the implant, and be partially or wholly released into fluid or tissue surrounding the implant. Degradation of the liberated polysaccharide by a carbohydrase can take place during or after liberation of the polysaccharide.

Degradation of the hydrophobic derivatives of the biodegradable polysaccharides of the present invention can result in the release of naturally occurring mono- or disaccharides, such as glucose. This is advantageous, particularly when these hydrophobic derivatives are used to form an implantable medical article, or a portion thereof. These naturally occurring mono- or disaccharides which are common serum components and present little or no immunogenic or toxic risk to the individual.

Optionally, a lipase can be used in association with the implant to accelerate degradation of the bond between the groups that include the hydrocarbon segment and the polysaccharide (e.g., ester bond).

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Example 1

11 g of dried maltodextrin (GPC, Grain Processing Corporation, Muscatine, Iowa) was dissolved in 100 mls of dimethyl sulfoxide with stirring. When the solution was complete, 20 g (0.244 moles, 19.32 mls, Sigma-Aldrich) of 1-methylimidizole followed by 50 g (0.32 moles, 52 mls, Sigma-Aldrich, Milwaukee, Wis.) of butyric anhydride were added with stirring at room temperature. The reaction solution was stirred for one hour and was then quenched with deionized water. The taffy-like material that precipitated from the quenched reaction mixture was placed in 1,000 MWCO dialysis tubing and dialyzed vs. continuous flow deionized water for three days. After this time the solid product was lyophilized. 23.169 g of a white powdery solid was obtained. The theoretical degree of substitution (DS) was 2.5.

Example 2

11 g of dried maltodextrin (MD) was dissolved in 100 mls of dimethyl sulfoxide with stirring. When the solution was complete, 20 g (0.244 moles, 19.32 mls) of 1-methylimidizole followed by 50 g (0.32 moles, 52 mls) of butyric anhydride were added with stirring at room temperature. The reaction solution was stirred for one hour and was then quenched with deionized water. The taffy-like material that precipitated from the quenched reaction mixture was placed in 1,000 MWCO dialysis tubing and dialyzed vs. continuous flow deionized water for three days. After this time the solid product was dried under vacuum. 22.8 g of a white powdery solid was obtained. The theoretical DS was 2.5.

Example 3

10 g of dried MD was dissolved in 100 mls of dimethyl sulfoxide with stirring. When the solution was complete, 23.7 g (0.29 moles, 22.9 mls) of 1-methylimidizole followed by 29.34 g (0.29 moles, 27.16 mls) of acetic anhydride (Sigma-Aldrich, Milwaukee, Wis.) were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid was collected via filtration and dried in vacuo. 15.92 g of a yellow powdery solid was obtained. The theoretical DS was 2.5

Example 4

10 g of dried MD was dissolved in 100 mls of dimethyl sulfoxide with stirring. When the solution was complete, 9.49 g (0.11 moles, 9.17 mls) of 1-methylimidizole followed by 18.19 g (0.11 moles, 18.81 mls) of butyric anhydride were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid was collected via filtration and dried in vacuo. 16.11 g of a white powdery solid was obtained. The theoretical DS was 1.

Example 5

10 g of dried MD was dissolved in 100 mls of dimethyl sulfoxide with stirring. When the solution was complete, 14.24 g (0.17 moles, 13.76 mls) of 1-methylimidizole followed by 27.32 g (0.17 moles, 28.25 mls) of butyric anhydride were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid was collected via filtration and dried in vacuo. 18.95 g of a white powdery solid was obtained. The theoretical DS was 1.5.

Example 6

10 g of dried MD was dissolved in 100 mls of dimethyl sulfoxide with stirring. When the solution was complete, 18.97 g (0.23 moles, 18.33 mls) of 1-methylimidizole followed by 36.39 g (0.23 moles, 37.63 mls) of butyric anhydride were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid was collected via filtration and dried in vacuo. 19.78 g of a white powdery solid was obtained. The theoretical DS was 2.

Example 7

10 g of dried polyalditol (GPC, Grain Processing Corporation, Muscatine, Iowa) was dissolved in 100 mls of dimethyl sulfoxide with stirring. When the solution was complete, 28.46 g (0.35 moles, 27.5 mls) of 1-methylimidizole followed by 54.58 g (0.35 moles, 56.44 mls) of butyric anhydride were added with stirring at room temperature. The reaction solution was stirred for one hour and was then quenched with deionized water. The reaction mixture was placed in 1,000 MWCO dialysis tubing and dialyzed vs. continuous flow deionized water for three days. After this time the solution was lyophilized. 11.55 g of a white powdery solid was obtained. The theoretical DS was 2.

Example 8

1 g of dried β-cyclodextrin (Sigma-Aldrich, Milwaukee, Wis.) was dissolved in 10 mls of dimethyl sulfoxide with stirring. When the solution was complete, 5.02 g (0.061 moles, 4.85 mls) of 1-methylimidizole followed by 9.62 g (0.061 moles, 9.95 mls) of butyric anhydride were added with stirring at room temperature. The reaction solution was stirred for one hour and was then quenched with deionized water. The reaction mixture was placed in 1,000 MWCO dialysis tubing and dialyzed vs. continuous flow deionized water for three days. After this time the solution was lyophilized. 234 mg of a white powdery solid was obtained. The theoretical DS was 2.

Example 9

10 g of dried MD was dissolved in 100 mls of dimethyl sulfoxide with stirring. When the solution was complete, 23.7 g (0.29 moles, 22.9 mls) of 1-methylimidizole followed by 37.38 g (0.29 moles, 36.8 mls) of propionic anhydride were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid was collected via filtration and dried in vacuo. 18.49 g of a white powdery solid was obtained. The theoretical DS was 2.5.

Example 10

10 g of dried MD was dissolved in 100 mls of dimethyl sulfoxide with stirring. When the solution was complete, 9.48 g (0.12 moles, 9.16 mls) of 1-methylimidizole followed by 14.95 g (0.12 moles, 14.73 mls) of propionoic anhydride were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid was collected via filtration and dried in vacuo. 14.32 g of a white powdery solid was obtained. The theoretical DS was 1.

Example 11

4 g of dried MD was dissolved in 40 mls of dimethyl sulfoxide with stirring. When the solution was complete, 9.48 g (0.12 moles, 9.16 mls) of 1-methylimidizole followed by 24.63 g (0.12 moles, 26.6 mls) of caproic anhydride were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid obtained was taffy-like and collected via filtration and dried in vacuo. 7.18 g of a white solid was obtained. The theoretical DS was 2.5.

Example 12

4 g of dried MD was dissolved in 40 mls of dimethyl sulfoxide with stirring. When the solution was complete, 3.79 g (0.046 moles, 3.7 mls) of 1-methylimidizole followed by 9.85 g (0.046 moles, 10.64 mls) of caproic anhydride were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid was collected via filtration and dried in vacuo. 9.02 g of a white powdery solid was obtained. The theoretical DS was 1.

Example 13

2.0 g of dried MD was dissolved in 10 mls of dimethyl sulfoxide with stirring. 0.751 g (2.3 mmole) decanoic anhydride was dissolved in 3 ml of chloroform. When the solutions were complete 0.188 g (2.3 mmoles, 0.183 mls) of 1-methylimidizole was added to the DMSO/MD solution followed by the addition of the chloroform/anhydride solution and 7.0 ml DMSO. The reaction was stirred for 1 hour at room temperature. The reaction mixture was placed in 1,000 MWCO dialysis tubing and dialyzed vs. continuous flow deionized water for three days. The dialysis tube and contents were placed in 1 liter of acetone/methanol-50/50 (volume) three times for more than 1 hour for each solvent change. The dialysis tube and contents were then placed in 4 liters of acetone/methanol-50/50 (volume) three times for 1 day for each solvent change. The solid from the dialysis tube was dried in vacuo. 1.69 g of a white solid was obtained. The theoretical DS was 0.1.

Example 14

5.0 g of dried MD was dissolved in 10 mls of dimethyl sulfoxide with stirring. 3.15 g (5.75 mmole) stearic anhydride was dissolved in 3 ml of chloroform. When the solutions were complete 0.472 g (5.75 mmoles, 0.458 mls) of 1-methylimidizole was added to the DMSO/MD solution followed by the addition of the chloroform/anhydride solution and 7.0 ml DMSO. The reaction was stirred for 1 hour at room temperature. The reaction mixture was placed in 1,000 MWCO dialysis tubing and dialyzed vs. continuous flow deionized water for three days. The dialysis tube and contents were placed in 1 liter of acetone/methanol-50/50 (volume) three times for more than 1 hour for each solvent change. The dialysis tube and contents were then placed in 4 liters of acetone/methanol-50/50 (volume) three times for 1 day for each solvent change. The solid from the dialysis tube was dried in vacuo. 6.58 g of a white powdery solid was obtained. The theoretical DS was 0.1.

Example 15

4 g of dried MD was dissolved in 40 mls of dimethyl sulfoxide with stirring. When the solution was complete, 9.48 g (0.12 moles, 9.16 mls) of 1-methylimidizole followed by 24.63 g (0.12 moles, 26.6 mls) of caproic anhydride were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid obtained was taffy-like and collected via filtration and dried in vacuo. 7.18 g of a white solid was obtained. The theoretical DS was 2.5.

Example 16

4 g of dried MD was dissolved in 40 mls of dimethyl sulfoxide with stirring. When the solution was complete, 9.48 g (0.12 moles, 9.16 mls) of 1-methylimidizole followed by 24.63 g (0.12 moles, 26.6 mls) of heptanoic anhydride were added with stirring at room temperature. The reaction solution was stirred for one hour and was then slowly add to 750 mls of deionized water in a Waring blender. The precipitated solid was collected via filtration, re-suspended in 1 L of deionized water and stirred for one hour. The solid obtained was taffy-like and collected via filtration and dried in vacuo. 7.18 g of a white solid was obtained. The theoretical DS was 2.5.

Example 17

Vacuum oven-dried Polyalditol PD60 (4.10 g), N-hydroxysuccinimide (0.38 g), 4-di(methylamino)pyridine (0.39 g), and 2-propylpentanoic acid (9.01 g) were weighed into a 120 mL amber vial. Anhydrous dimethyl sulfoxide, DMSO, (50 mL) was poured into the vial, purged with nitrogen, and placed on a rotary shaker to dissolve. N,N'-diisopropylcarbodiimide, DIC, (9.47 g) was weighed into a 30 mL amber vial and dissolved with 10 mL of anhydrous DMSO. The DIC solution was poured into the 120 mL amber vial and purged with nitrogen gas. A Teflon stir bar was inserted into the 120 mL vial before being capped and placed on a stir plate to stir overnight at room temperature. After overnight stirring, no visible product was seen and the reaction was placed in a 55° C. oven to stir overnight. The reaction formed two layers after heating overnight and was precipitated into 2 L deionized water while stirring. The yellowish/white solid was vacuum-filtered using a water aspirator and rinsed three times with deionized water (100 mL). The solid precipitate was collected and dried in a vacuum oven at 40° C. overnight. The dried solid was organic soluble (tetrahydrofuran, methylene chloride). A 50 mg/mL solution in THF was prepared and tested by dip coating onto a clean Pebax rod giving a uniform, off-white coating.

Example 18

Vacuum oven-dried Polyalditol PD60 (4.10 g), N-hydroxysuccinimide (0.38 g), 4-di(methylamino)pyridine (0.39 g), and o-acetylsalicylic acid, ASA, (11.26 g) were weighed into a 120 mL amber vial. Anhydrous dimethyl sulfoxide (50 mL) was poured into the vial, purged with nitrogen, and placed on a rotary shaker to dissolve. N,N'-diisopropylcarbodiimide, DIC, (9.47 g) was weighed into a 30 mL amber vial and dissolved with 10 mL of anhydrous DMSO. The DIC solution was poured into the 120 mL amber vial and purged with nitrogen gas. A Teflon stir bar was inserted into the 120 mL vial before being capped and placed on a stir plate to stir overnight at room temperature. After overnight stirring, no visible product was seen and the reaction was placed in a 55° C. oven to stir overnight. The reaction formed a viscous, orange material after heating overnight and was precipitated into 2 L deionized water while stirring. The orange solid was vacuum-filtered using a water aspirator and rinsed once with acetone (25 mL) followed by three times with deionized water (100 mL). The solid precipitate was collected and dried in a vacuum oven at 40° C. overnight. The dried solid was organic soluble (tetrahydrofuran, methylene chloride).

Example 19

Preparation of Hydrophobic MD-Triamcinolone Implants

Triamcinolone acetonide-releasing medical implants were prepared by combining various hydrophobic maltodextrin (MD) polymers with triamcinolone acetonide (TA) in various ratios. In some cases a hydrophilic polymer was added to the hydrophobic MD and TA. Implants were prepared using hydrophobic MDs, TA, and hydrophilic polymers in the amounts as shown in Table 1.

The ingredients were heated and mixed in an extruder (DACA™ Microcompounder; DACA Instruments, Santa Barbara Calif.). Total batch size for an individual preparation was 4 grams. For example 2 g of MD-Hex (DS 2.5) ~3 kDa was mixed with 2 g of triamcinolone acetonide (Pharmacia & Upjohn Company) the preparation of implant sample A. Ingredients were fed in dry (powder of pellet) form to the feed section of the heated extruder. For preparations containing MD-But 2.0 the extruder was heated to a temperature of approximately 150° C. For preparations containing MD-But 2.0 the extruder was heated to a temperature of approximately 150° C. For preparations containing MD-Hex 2.5, MD-Hep 2.5, or if the preparation included a hydrophilic polymer, the extruder was heated to a temperature of approximately 110° C. The extruder heated, mixed, and recirculated the ingredients to create a uniform mixture. The polymeric ingredients melted and blended together, and the TA is uniformly blended into the polymer melt. Processing temperatures did not melt PVP in the PVP-containing mixtures. The ingredients were mixed for an average of about 6 minutes before being extruded. Solvent was not added, so the original polymorphic form of the TA during the extrusion process was maintained. After melting and mixing, the mixture was extruded out of a die and elongated into a cylindrical shape with diameter in the range of about 250 µm to about 650 µm. Other diameters, such in the range of about 100 µn to 1000 µm, can be prepared. Upon cooling and solidification, the resulting cylinders were cut to the desired length, typically 3-6 mm, to create the implant.

FIG. 5 illustrates x-ray diffraction (XRD) spectra of various hydrophobic maltodextrin-based pellets showing peaks corresponding to non-polymorphic and polymorphic forms of TA in the pellets.

TABLE 1

| Sample | Hydrophobic Polysaccharide Type | amount | TA amount | Polymeric Additive type | Amount |
|---|---|---|---|---|---|
| A | MD-Hex (DS 2.5) DE5 | 50% wt/wt | 50% wt/wt | (—) | |
| B | MD-Hep (DS 2.5) DE5 | 50% wt/wt | 50% wt/wt | (—) | |
| C | MD-Hex (DS 2.5) DE10 | 50% wt/wt | 50% wt/wt | (—) | |
| traD | MD-Hex (DS 2.5) DE5 | 50% wt/wt | 40% wt/wt | PVP 30 kDa | 10% wt/wt |
| E | MD-Hep (DS 2.5) DE5 | 50% wt/wt | 40% wt/wt | PVP 30 kDa | 10% wt/wt |
| F | MD-Hex (DS 2.5) DE5 | 50% wt/wt | 40% wt/wt | PEG 20 kDa | 10% wt/wt |
| G | MD-Hep (DS 2.5) DE5 | 50% wt/wt | 40% wt/wt | PEG 20 kDa | 10% wt/wt |
| H | MD-Hex (DS 2.5) DE10 | 50% wt/wt | 40% wt/wt | PEG 20 kDa | 10% wt/wt |
| I | MD-Pro (DS 2.5) DE5 | 70% wt/wt | 30% wt/wt | (—) | |
| J | MD-But (DS 2.0) DE5 | 50% wt/wt | 50% wt/wt | (—) | |
| K | MD-But (DS 2.0) DE5 | 70% wt/wt | 30% wt/wt | (—) | |
| L | MD-Hex (DS 2.5) DE5 | 70% wt/wt | 30% wt/wt | (—) | |

Example 20

Triamcinolone Acetonide Release from Implants

Release of the TA was examined by placing an implant in 4 mLs of phosphate buffered saline (pH 7.4) with agitation on an orbital shaking platform at 37° C. At appropriate time points of 1 hr, 3 hr, 6 hr, 3 days, 7 days, 14 days, 21 days, 28 days, 35 days, 42 days, 49 days, 56 days, 63 days, 76 days, 90 days, 104 days, 119 days, 134 days, 148 days the PBS was removed and replaced with fresh PBS. (FIGS. 1 A & B, 2 A & B, and 3). For data shown in FIGS. 4 A & B, measurement after 21 days were taken every two weeks. The concentration of active agent in the removed PBS was then quantified by UV VIS spectroscopy. Results of TA release are shown in FIGS. 1-4.

What is claimed is:

1. A biodegradable bioactive-agent releasing medical implant comprising a matrix comprising a hydrophobic derivative of an α(1→4)glucopyranose polymer and bioactive-agent within the matrix, wherein the bioactive agent is capable of being released from the implant following placement of the implant in a subject.

2. The medical implant of claim 1 wherein the hydrophobic derivative of the α(1→4)glucopyranose polymer has an average molecular weight of 500,000 Da or less.

3. The medical implant of claim 2 wherein the hydrophobic derivative of the α(1→4)glucopyranose polymer has an average molecular weight of 100,000 Da or less.

4. The medical implant of claim 3 wherein the hydrophobic derivative of the α(1→4)glucopyranose polymer has an average molecular weight of 50,000 Da or less.

5. The medical implant of claim 4 wherein the hydrophobic derivative of the α(1→4)glucopyranose polymer has an average molecular weight in the range of 2000 Da to 20,000 Da.

6. The medical implant of claim 5 wherein the hydrophobic derivative of the α(1→4)glucopyranose polymer has an average molecular weight in the range of 4000 Da to 10,000 Da.

7. The medical implant of claim 1 wherein the hydrophobic derivative of the α(1→4)glucopyranose polymer comprises a plurality of groups pendent from a poly-α(1→4)glucopyranose backbone, the groups comprising a hydrocarbon segment selected from the group consisting of linear, branched, and cyclic $C_2$-$C_{18}$ groups.

8. The medical implant of claim 7 wherein the hydrocarbon segment is selected from the group consisting of linear, branched, and cyclic $C_4$-$C_{10}$ groups.

9. The medical implant of claim 8 wherein the hydrocarbon segment is selected from the group consisting of linear, branched, or cyclic $C_5$-$C_7$ groups.

10. The medical implant of claim 9 wherein the plurality of groups pendent from the polysaccharide backbone provide a degree of substitution in the range of 2-3.

11. The medical implant of claim 10 wherein the hydrocarbon segment is a linear $C_6$ group.

12. The medical implant of claim 7 wherein the plurality of groups pendent from the polysaccharide backbone provide a degree of substitution in the range of 0.5-1.5.

13. The medical implant of claim 1 wherein the hydrophobic derivatives have a Tg of 35° C. or greater.

14. The medical implant of claim 13 wherein the hydrophobic derivatives have a Tg in the range of 40° C. to 60° C.

15. The medical implant of claim 1 wherein the hydrophobic derivatives are present in the implant in an amount in the range of 35 wt % to 90 wt %.

16. The medical implant of claim 15 wherein the hydrophobic derivatives are present in the implant in an amount in the range of 35 wt % to 60 wt %.

17. The medical implant of claim 1 further comprising a biocompatible hydrophilic polymer.

18. The medical implant of claim 17 wherein the biocompatible hydrophilic polymer is selected from the group consisting of group consisting of poly(ethylene glycol), hydrophilic polysaccharides, polyvinyl pyrrolidones, polyvinyl alcohols, low molecular weight methyl cellulose, and hydroxypropyl methyl cellulose (HPMC).

19. The medical implant of claim 18 wherein the biocompatible hydrophilic polymer is present in the implant in an amount in the range of 1 wt % to 20 wt %.

20. The medical implant of claim 1 wherein the bioactive agent is present in the implant in an amount in the range of 10 wt % to 65 wt %.

21. The medical implant of claim 1 wherein the bioactive agent comprises a compound useful for treating an ocular condition.

22. The medical implant of claim 1 wherein the bioactive agent is present in a single polymorphic form.

23. The medical implant of claim 1 wherein the bioactive agent is coupled to a polysaccharide backbone of the hydrophobic derivatives via a hydrolyzable ester bond.

24. The medical implant of claim 1 wherein the bioactive agent is capable of being released from the implant in a form comprising a free carboxylate group.

25. A biodegradable implantable medical device comprising a matrix comprising a hydrophobic derivative of an α(1→4)glucopyranose polymer, wherein the device has a structure that is useful for treating a medical condition following placement of the device in a subject.

26. The medical implant of claim 1 which is in a form selected from the group consisting of rods, pellets, disks, spheres, strips, and coils.

27. The medical implant of claim 1 which is in a form of a microparticle.

28. The medical implant of claim 1 which is in a form of a filament.

29. The medical implant of claim 1 which has a diameter in the range of 100 μM to 1000 μM.

30. The medical implant of claim 1 wherein the hydrophobic derivative of the α(1→4)glucopyranose polymer is formed a polymer selected from the group consisting of maltodextrin, polyalditol, amylose, and cyclodextrin.

31. The medical implant of claim 30 wherein the hydrophobic derivative of the α(1→4)glucopyranose polymer is formed from maltodextrin.

32. The medical implant of claim 1 wherein the hydrophobic derivative of the α(1→4)glucopyranose polymer comprises a plurality of groups pendent from its polymer backbone, the groups comprising a hydrocarbon segment and a chemical group linking the hydrocarbon segment to a monomeric unit of the polymer backbone, the chemical linking group comprising a hydrolytically cleavable covalent bond.

33. The medical implant of claim 1 wherein the hydrophobic derivative of the α(1→4)glucopyranose polymer is formed by the reaction of an α(1→4)glucopyranose polymer with a compound that includes a hydrocarbon segment and a hydroxyl-reactive group.

34. The medical implant of claim 33 wherein the hydroxyl-reactive group is selected from the group consisting of acetal, carboxyl, anhydride, and acid halide.

* * * * *